(12) United States Patent
Singh

(10) Patent No.: US 8,402,326 B2
(45) Date of Patent: *Mar. 19, 2013

(54) INTEGRATED CIRCUIT HAVING MEMORY ARRAY INCLUDING ECC AND COLUMN REDUNDANCY AND METHOD OF OPERATING SAME

(75) Inventor: Anant Pratap Singh, Portland, OR (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/306,642

(22) Filed: Nov. 29, 2011

(65) Prior Publication Data

US 2012/0134216 A1 May 31, 2012

Related U.S. Application Data

(63) Continuation of application No. 11/821,469, filed on Jun. 22, 2007, now Pat. No. 8,069,377.

(60) Provisional application No. 60/816,416, filed on Jun. 26, 2006.

(51) Int. Cl.
*G11C 29/00* (2006.01)
(52) U.S. Cl. ...................................... 714/711
(58) Field of Classification Search .......... 714/710, 714/711, 758, 763
See application file for complete search history.

(56) References Cited

U.S. PATENT DOCUMENTS

| | | | |
|---|---|---|---|
| 3,439,214 A | 4/1969 | Kabell | |
| 3,997,799 A | 12/1976 | Baker | |
| 4,032,947 A | 6/1977 | Kesel et al. | |
| 4,250,569 A | 2/1981 | Sasaki et al. | |
| 4,262,340 A | 4/1981 | Sasaki et al. | |
| 4,298,962 A | 11/1981 | Hamano et al. | |
| 4,371,955 A | 2/1983 | Sasaki | |
| 4,527,181 A | 7/1985 | Sasaki | |
| 4,630,089 A | 12/1986 | Sasaki et al. | |
| 4,631,725 A * | 12/1986 | Takamura et al. | ............ 714/752 |
| 4,658,377 A | 4/1987 | McElroy | |
| 4,692,923 A | 9/1987 | Poeppelman | |

(Continued)

FOREIGN PATENT DOCUMENTS

| | | |
|---|---|---|
| CA | 272437 | 7/1927 |
| EP | 0 030 856 | 6/1981 |

(Continued)

OTHER PUBLICATIONS

Arimoto et al., A Configurable Enhanced T2RAM Macro for System-Level Power Management Unified Memory, 2006, VLSI Symposium.

(Continued)

*Primary Examiner* — James C Kerveros
(74) *Attorney, Agent, or Firm* — Wilmer Cutler Pickering Hale and Dorr LLP

(57) ABSTRACT

An integrated circuit device comprising a memory cell array having a plurality of memory cells arranged in a matrix of rows and columns; multiplexer circuitry, coupled to the memory cell array, comprising a plurality of data multiplexers, each data multiplexer having a plurality of inputs, comprising (i) a first input to receive write data which is representative of data to be written into the memory cells of the memory cell array in response to a write operation, and (ii) a second input to receive read data which is representative of data read from memory cells of the memory cell array, and an associated output to responsively output data from one of the plurality of inputs; and syndrome generation circuitry, coupled to the multiplexer circuitry, to generate: (i) a write data syndrome vector using the write data and (ii) a read data syndrome vector using the read data.

21 Claims, 21 Drawing Sheets

U.S. PATENT DOCUMENTS

| | | | |
|---|---|---|---|
| 4,710,934 A | 12/1987 | Traynor | |
| 4,791,610 A | 12/1988 | Takemae | |
| 4,807,195 A | 2/1989 | Busch et al. | |
| 4,954,989 A | 9/1990 | Auberton-Herve et al. | |
| 4,979,014 A | 12/1990 | Hieda et al. | |
| 5,010,524 A | 4/1991 | Fifield et al. | |
| 5,134,616 A | 7/1992 | Barth et al. | |
| 5,144,390 A | 9/1992 | Matloubian | |
| 5,164,805 A | 11/1992 | Lee | |
| 5,258,635 A | 11/1993 | Nitayama et al. | |
| 5,313,432 A | 5/1994 | Lin et al. | |
| 5,315,541 A | 5/1994 | Harari et al. | |
| 5,350,938 A | 9/1994 | Matsukawa | |
| 5,355,330 A | 10/1994 | Hisamoto et al. | |
| 5,381,424 A * | 1/1995 | Tsang | 714/769 |
| 5,388,068 A | 2/1995 | Ghoshal et al. | |
| 5,397,726 A | 3/1995 | Bergemont et al. | |
| 5,432,730 A | 7/1995 | Shubat et al. | |
| 5,446,299 A | 8/1995 | Acovic et al. | |
| 5,448,513 A | 9/1995 | Hu et al. | |
| 5,466,625 A | 11/1995 | Hsieh et al. | |
| 5,489,792 A | 2/1996 | Hu et al. | |
| 5,506,436 A | 4/1996 | Hayashi et al. | |
| 5,515,383 A | 5/1996 | Katoozi | |
| 5,526,307 A | 6/1996 | Yiu et al. | |
| 5,528,062 A | 6/1996 | Hsieh et al. | |
| 5,568,356 A | 10/1996 | Schwartz | |
| 5,583,808 A | 12/1996 | Brahmbhatt | |
| 5,593,912 A | 1/1997 | Rajeevakumar | |
| 5,606,188 A | 2/1997 | Bronner et al. | |
| 5,608,250 A | 3/1997 | Kalnitsky | |
| 5,627,092 A | 5/1997 | Alsmeier et al. | |
| 5,631,186 A | 5/1997 | Park et al. | |
| 5,677,867 A | 10/1997 | Hazani | |
| 5,696,718 A | 12/1997 | Hartmann | |
| 5,740,099 A | 4/1998 | Tanigawa | |
| 5,754,469 A | 5/1998 | Hung et al. | |
| 5,774,411 A | 6/1998 | Hsieh et al. | |
| 5,778,243 A | 7/1998 | Aipperspach et al. | |
| 5,780,906 A | 7/1998 | Wu et al. | |
| 5,784,311 A | 7/1998 | Assaderaghi et al. | |
| 5,798,968 A | 8/1998 | Lee et al. | |
| 5,811,283 A | 9/1998 | Sun | |
| 5,847,411 A | 12/1998 | Morii | |
| 5,877,978 A | 3/1999 | Morishita et al. | |
| 5,886,376 A | 3/1999 | Acovic et al. | |
| 5,886,385 A | 3/1999 | Arisumi et al. | |
| 5,897,351 A | 4/1999 | Forbes | |
| 5,929,479 A | 7/1999 | Oyama | |
| 5,930,648 A | 7/1999 | Yang | |
| 5,936,265 A | 8/1999 | Koga | |
| 5,939,745 A | 8/1999 | Park et al. | |
| 5,943,258 A | 8/1999 | Houston et al. | |
| 5,943,581 A | 8/1999 | Lu et al. | |
| 5,960,265 A | 9/1999 | Acovic et al. | |
| 5,968,840 A | 10/1999 | Park et al. | |
| 5,977,578 A | 11/1999 | Tang | |
| 5,982,003 A | 11/1999 | Hu et al. | |
| 5,986,914 A | 11/1999 | McClure | |
| 6,018,172 A | 1/2000 | Hidada et al. | |
| 6,048,756 A | 4/2000 | Lee et al. | |
| 6,081,443 A | 6/2000 | Morishita | |
| 6,096,598 A | 8/2000 | Furukawa et al. | |
| 6,097,056 A | 8/2000 | Hsu et al. | |
| 6,097,624 A | 8/2000 | Chung et al. | |
| 6,111,778 A | 8/2000 | MacDonald et al. | |
| 6,121,077 A | 9/2000 | Hu et al. | |
| 6,133,597 A | 10/2000 | Li et al. | |
| 6,157,216 A | 12/2000 | Lattimore et al. | |
| 6,163,871 A * | 12/2000 | Yang | 714/769 |
| 6,171,923 B1 | 1/2001 | Chi et al. | |
| 6,177,300 B1 | 1/2001 | Houston et al. | |
| 6,177,698 B1 | 1/2001 | Gruening et al. | |
| 6,177,708 B1 | 1/2001 | Kuang et al. | |
| 6,214,694 B1 | 4/2001 | Leobandung et al. | |
| 6,222,217 B1 | 4/2001 | Kunikiyo | |
| 6,225,158 B1 | 5/2001 | Furukawa et al. | |
| 6,245,613 B1 | 6/2001 | Hsu et al. | |
| 6,252,281 B1 | 6/2001 | Yamamoto et al. | |
| 6,262,935 B1 | 7/2001 | Parris et al. | |
| 6,292,424 B1 | 9/2001 | Ohsawa | |
| 6,297,090 B1 | 10/2001 | Kim | |
| 6,300,649 B1 | 10/2001 | Hu et al. | |
| 6,320,227 B1 | 11/2001 | Lee et al. | |
| 6,333,532 B1 | 12/2001 | Davari et al. | |
| 6,333,866 B1 | 12/2001 | Ogata | |
| 6,350,653 B1 | 2/2002 | Adkisson et al. | |
| 6,351,426 B1 | 2/2002 | Ohsawa | |
| 6,359,802 B1 | 3/2002 | Lu et al. | |
| 6,360,347 B1 * | 3/2002 | Walters, Jr. | 714/763 |
| 6,384,445 B1 | 5/2002 | Hidaka et al. | |
| 6,391,658 B1 | 5/2002 | Gates et al. | |
| 6,403,435 B1 | 6/2002 | Kang et al. | |
| 6,421,269 B1 | 7/2002 | Somasekhar et al. | |
| 6,424,011 B1 | 7/2002 | Assaderaghi et al. | |
| 6,424,016 B1 | 7/2002 | Houston | |
| 6,429,477 B1 | 8/2002 | Mandelman et al. | |
| 6,432,769 B1 | 8/2002 | Fukuda et al. | |
| 6,440,872 B1 | 8/2002 | Mandelman et al. | |
| 6,441,435 B1 | 8/2002 | Chan | |
| 6,441,436 B1 | 8/2002 | Wu et al. | |
| 6,466,511 B2 | 10/2002 | Fujita et al. | |
| 6,479,862 B1 | 11/2002 | King et al. | |
| 6,480,407 B1 | 11/2002 | Keeth | |
| 6,492,211 B1 | 12/2002 | Divakaruni et al. | |
| 6,516,443 B1 * | 2/2003 | Zook | 714/792 |
| 6,518,105 B1 | 2/2003 | Yang et al. | |
| 6,531,754 B1 | 3/2003 | Nagano et al. | |
| 6,537,871 B2 | 3/2003 | Forbes | |
| 6,538,916 B2 | 3/2003 | Ohsawa | |
| 6,544,837 B1 | 4/2003 | Divakaruni et al. | |
| 6,548,848 B2 | 4/2003 | Horiguchi et al. | |
| 6,549,450 B1 | 4/2003 | Hsu et al. | |
| 6,552,398 B2 | 4/2003 | Hsu et al. | |
| 6,552,932 B1 | 4/2003 | Cernea | |
| 6,556,477 B2 | 4/2003 | Hsu et al. | |
| 6,560,142 B1 | 5/2003 | Ando | |
| 6,563,733 B2 | 5/2003 | Liu et al. | |
| 6,566,177 B1 | 5/2003 | Radens et al. | |
| 6,567,330 B2 | 5/2003 | Fujita et al. | |
| 6,573,566 B2 | 6/2003 | Ker et al. | |
| 6,574,135 B1 | 6/2003 | Komatsuzaki | |
| 6,590,258 B2 | 7/2003 | Divakauni et al. | |
| 6,590,259 B2 | 7/2003 | Adkisson et al. | |
| 6,617,651 B2 | 9/2003 | Ohsawa | |
| 6,621,725 B2 | 9/2003 | Ohsawa | |
| 6,632,723 B2 | 10/2003 | Watanabe et al. | |
| 6,650,565 B1 | 11/2003 | Ohsawa | |
| 6,653,175 B1 | 11/2003 | Nemati et al. | |
| 6,678,860 B1 | 1/2004 | Lee | |
| 6,686,624 B2 | 2/2004 | Hsu | |
| 6,703,673 B2 | 3/2004 | Houston | |
| 6,707,118 B2 | 3/2004 | Muljono et al. | |
| 6,714,436 B1 | 3/2004 | Burnett et al. | |
| 6,721,222 B2 | 4/2004 | Somasekhar et al. | |
| 6,825,524 B1 | 11/2004 | Ikehashi et al. | |
| 6,861,689 B2 | 3/2005 | Burnett | |
| 6,870,225 B2 | 3/2005 | Bryant et al. | |
| 6,882,566 B2 | 4/2005 | Nejad et al. | |
| 6,888,770 B2 | 5/2005 | Ikehashi | |
| 6,894,913 B2 | 5/2005 | Yamauchi | |
| 6,897,098 B2 | 5/2005 | Hareland et al. | |
| 6,903,984 B1 | 6/2005 | Tang et al. | |
| 6,909,151 B2 | 6/2005 | Hareland et al. | |
| 6,912,150 B2 | 6/2005 | Portmann et al. | |
| 6,913,964 B2 | 7/2005 | Hsu | |
| 6,936,508 B2 | 8/2005 | Visokay et al. | |
| 6,969,662 B2 | 11/2005 | Fazan et al. | |
| 6,973,613 B2 | 12/2005 | Cypher | |
| 6,975,536 B2 | 12/2005 | Maayan et al. | |
| 6,982,902 B2 | 1/2006 | Gogl et al. | |
| 6,987,041 B2 | 1/2006 | Ohkawa | |
| 7,030,436 B2 | 4/2006 | Forbes | |
| 7,037,790 B2 | 5/2006 | Chang et al. | |
| 7,041,538 B2 | 5/2006 | Ieong et al. | |
| 7,042,765 B2 | 5/2006 | Sibigtroth et al. | |
| 7,061,806 B2 | 6/2006 | Tang et al. | |

| | | |
|---|---|---|
| 7,085,153 B2 | 8/2006 | Ferrant et al. |
| 7,085,156 B2 | 8/2006 | Ferrant et al. |
| 7,085,971 B2 | 8/2006 | Barth et al. |
| 7,170,807 B2 | 1/2007 | Fazan et al. |
| 7,177,175 B2 | 2/2007 | Fazan et al. |
| 7,187,581 B2 | 3/2007 | Ferrant et al. |
| 7,203,115 B2 | 4/2007 | Eto |
| 7,228,468 B2 | 6/2007 | Wu et al. |
| 7,230,846 B2 | 6/2007 | Keshavarzi |
| 7,233,024 B2 | 6/2007 | Scheuerlein et al. |
| 7,256,459 B2 | 8/2007 | Shino |
| 7,301,803 B2 | 11/2007 | Okhonin et al. |
| 7,301,838 B2 | 11/2007 | Waller |
| 7,317,641 B2 | 1/2008 | Scheuerlein |
| 7,324,387 B1 | 1/2008 | Bergemont et al. |
| 7,335,934 B2 | 2/2008 | Fazan |
| 7,341,904 B2 | 3/2008 | Willer |
| 7,392,456 B2 * | 6/2008 | Leung et al. .................. 714/763 |
| 7,416,943 B2 | 8/2008 | Figura et al. |
| 7,456,439 B1 | 11/2008 | Horch |
| 7,477,540 B2 | 1/2009 | Okhonin et al. |
| 7,492,632 B2 | 2/2009 | Carman |
| 7,517,744 B2 | 4/2009 | Mathew et al. |
| 7,539,041 B2 | 5/2009 | Kim et al. |
| 7,542,340 B2 | 6/2009 | Fisch et al. |
| 7,542,345 B2 | 6/2009 | Okhonin et al. |
| 7,545,694 B2 | 6/2009 | Srinivasa Raghavan et al. |
| 7,606,066 B2 | 10/2009 | Okhonin et al. |
| 7,634,713 B1 | 12/2009 | Ngo |
| 7,696,032 B2 | 4/2010 | Kim et al. |
| 2001/0055859 A1 | 12/2001 | Yamada et al. |
| 2002/0030214 A1 | 3/2002 | Horiguchi |
| 2002/0034855 A1 | 3/2002 | Horiguchi et al. |
| 2002/0036322 A1 | 3/2002 | Divakauni et al. |
| 2002/0051378 A1 | 5/2002 | Ohsawa |
| 2002/0064913 A1 | 5/2002 | Adkisson et al. |
| 2002/0070411 A1 | 6/2002 | Vermandel et al. |
| 2002/0072155 A1 | 6/2002 | Liu et al. |
| 2002/0076880 A1 | 6/2002 | Yamada et al. |
| 2002/0086463 A1 | 7/2002 | Houston et al. |
| 2002/0089038 A1 | 7/2002 | Ning |
| 2002/0098643 A1 | 7/2002 | Kawanaka et al. |
| 2002/0110018 A1 | 8/2002 | Ohsawa |
| 2002/0114191 A1 | 8/2002 | Iwata et al. |
| 2002/0130341 A1 | 9/2002 | Horiguchi et al. |
| 2002/0160581 A1 | 10/2002 | Watanabe et al. |
| 2002/0180069 A1 | 12/2002 | Houston |
| 2003/0003608 A1 | 1/2003 | Arikado et al. |
| 2003/0015757 A1 | 1/2003 | Ohsawa |
| 2003/0035324 A1 | 2/2003 | Fujita et al. |
| 2003/0042516 A1 | 3/2003 | Forbes et al. |
| 2003/0047784 A1 | 3/2003 | Matsumoto et al. |
| 2003/0057487 A1 | 3/2003 | Yamada et al. |
| 2003/0057490 A1 | 3/2003 | Nagano et al. |
| 2003/0102497 A1 | 6/2003 | Fried et al. |
| 2003/0112659 A1 | 6/2003 | Ohsawa |
| 2003/0123279 A1 | 7/2003 | Aipperspach et al. |
| 2003/0146474 A1 | 8/2003 | Ker et al. |
| 2003/0146488 A1 | 8/2003 | Nagano et al. |
| 2003/0151112 A1 | 8/2003 | Yamada et al. |
| 2003/0231521 A1 | 12/2003 | Ohsawa |
| 2004/0021137 A1 | 2/2004 | Fazan et al. |
| 2004/0021179 A1 | 2/2004 | Lee |
| 2004/0029335 A1 | 2/2004 | Lee et al. |
| 2004/0075143 A1 | 4/2004 | Bae et al. |
| 2004/0108532 A1 | 6/2004 | Forbes et al. |
| 2004/0188714 A1 | 9/2004 | Scheuerlein et al. |
| 2004/0217420 A1 | 11/2004 | Yeo et al. |
| 2005/0001257 A1 | 1/2005 | Schloesser et al. |
| 2005/0001269 A1 | 1/2005 | Hayashi et al. |
| 2005/0017240 A1 | 1/2005 | Fazan |
| 2005/0047240 A1 | 3/2005 | Ikehashi et al. |
| 2005/0062088 A1 | 3/2005 | Houston |
| 2005/0063224 A1 | 3/2005 | Fazan et al. |
| 2005/0064659 A1 | 3/2005 | Willer |
| 2005/0105342 A1 | 5/2005 | Tang et al. |
| 2005/0111255 A1 | 5/2005 | Tang et al. |
| 2005/0121710 A1 | 6/2005 | Shino |
| 2005/0135169 A1 | 6/2005 | Somasekhar et al. |
| 2005/0141262 A1 | 6/2005 | Yamada et al. |
| 2005/0141290 A1 | 6/2005 | Tang et al. |
| 2005/0145886 A1 | 7/2005 | Keshavarzi et al. |
| 2005/0145935 A1 | 7/2005 | Keshavarzi et al. |
| 2005/0167751 A1 | 8/2005 | Nakajima et al. |
| 2005/0189576 A1 | 9/2005 | Ohsawa |
| 2005/0208716 A1 | 9/2005 | Takaura et al. |
| 2005/0226070 A1 | 10/2005 | Ohsawa |
| 2005/0232043 A1 | 10/2005 | Ohsawa |
| 2005/0242396 A1 | 11/2005 | Park et al. |
| 2005/0265107 A1 | 12/2005 | Tanaka |
| 2006/0043484 A1 | 3/2006 | Cabral et al. |
| 2006/0084247 A1 | 4/2006 | Liu |
| 2006/0091462 A1 | 5/2006 | Okhonin et al. |
| 2006/0098481 A1 | 5/2006 | Okhonin et al. |
| 2006/0126374 A1 | 6/2006 | Waller et al. |
| 2006/0131650 A1 | 6/2006 | Okhonin et al. |
| 2006/0223302 A1 | 10/2006 | Chang et al. |
| 2007/0008811 A1 | 1/2007 | Keeth et al. |
| 2007/0023833 A1 | 2/2007 | Okhonin et al. |
| 2007/0045709 A1 | 3/2007 | Yang |
| 2007/0058427 A1 | 3/2007 | Okhonin et al. |
| 2007/0064489 A1 | 3/2007 | Bauser |
| 2007/0085140 A1 | 4/2007 | Bassin |
| 2007/0097751 A1 | 5/2007 | Popoff et al. |
| 2007/0114599 A1 | 5/2007 | Hshieh |
| 2007/0133330 A1 | 6/2007 | Ohsawa |
| 2007/0138524 A1 | 6/2007 | Kim et al. |
| 2007/0138530 A1 | 6/2007 | Okhonin |
| 2007/0187751 A1 | 8/2007 | Hu et al. |
| 2007/0187775 A1 | 8/2007 | Okhonin et al. |
| 2007/0200176 A1 | 8/2007 | Kammler et al. |
| 2007/0252205 A1 | 11/2007 | Hoentschel et al. |
| 2007/0263466 A1 | 11/2007 | Morishita et al. |
| 2007/0278578 A1 | 12/2007 | Yoshida |
| 2008/0049486 A1 | 2/2008 | Gruening-von Schwerin |
| 2008/0083949 A1 | 4/2008 | Zhu et al. |
| 2008/0099808 A1 | 5/2008 | Burnett et al. |
| 2008/0130379 A1 | 6/2008 | Ohsawa |
| 2008/0133849 A1 | 6/2008 | Demi et al. |
| 2008/0165577 A1 | 7/2008 | Fazan et al. |
| 2008/0253179 A1 | 10/2008 | Slesazeck |
| 2008/0258206 A1 | 10/2008 | Hofmann |
| 2009/0086535 A1 | 4/2009 | Ferrant et al. |
| 2009/0121269 A1 | 5/2009 | Caillat et al. |
| 2009/0127592 A1 | 5/2009 | El-Kareh et al. |
| 2009/0201723 A1 | 8/2009 | Okhonin et al. |
| 2010/0085813 A1 | 4/2010 | Shino |
| 2010/0091586 A1 | 4/2010 | Carman |
| 2010/0110816 A1 | 5/2010 | Nautiyal et al. |

FOREIGN PATENT DOCUMENTS

| | | |
|---|---|---|
| EP | 0 350 057 | 1/1990 |
| EP | 0 354 348 | 2/1990 |
| EP | 0 202 515 | 3/1991 |
| EP | 0 207 619 | 8/1991 |
| EP | 0 175 378 | 11/1991 |
| EP | 0 253 631 | 4/1992 |
| EP | 0 513 923 | 11/1992 |
| EP | 0 300 157 | 5/1993 |
| EP | 0 564 204 | 10/1993 |
| EP | 0 579 566 | 1/1994 |
| EP | 0 362 961 | 2/1994 |
| EP | 0 599 506 | 6/1994 |
| EP | 0 359 551 | 12/1994 |
| EP | 0 366 882 | 5/1995 |
| EP | 0 465 961 | 8/1995 |
| EP | 0 694 977 | 1/1996 |
| EP | 0 333 426 | 7/1996 |
| EP | 0 727 820 | 8/1996 |
| EP | 0 739 097 | 10/1996 |
| EP | 0 245 515 | 4/1997 |
| EP | 0 788 165 | 8/1997 |
| EP | 0 801 427 | 10/1997 |
| EP | 0 510 607 | 2/1998 |
| EP | 0 537 677 | 8/1998 |
| EP | 0 858 109 | 8/1998 |
| EP | 0 860 878 | 8/1998 |
| EP | 0 869 511 | 10/1998 |

| | | |
|---|---|---|
| EP | 0 878 804 | 11/1998 |
| EP | 0 920 059 | 6/1999 |
| EP | 0 924 766 | 6/1999 |
| EP | 0 642 173 | 7/1999 |
| EP | 0 727 822 | 8/1999 |
| EP | 0 933 820 | 8/1999 |
| EP | 0 951 072 | 10/1999 |
| EP | 0 971 360 | 1/2000 |
| EP | 0 980 101 | 2/2000 |
| EP | 0 601 590 | 4/2000 |
| EP | 0 993 037 | 4/2000 |
| EP | 0 836 194 | 5/2000 |
| EP | 0 599 388 | 8/2000 |
| EP | 0 689 252 | 8/2000 |
| EP | 0 606 758 | 9/2000 |
| EP | 0 682 370 | 9/2000 |
| EP | 1 073 121 | 1/2001 |
| EP | 0 726 601 | 9/2001 |
| EP | 0 731 972 | 11/2001 |
| EP | 1 162 663 | 12/2001 |
| EP | 1 162 744 | 12/2001 |
| EP | 1 179 850 | 2/2002 |
| EP | 1 180 799 | 2/2002 |
| EP | 1 191 596 | 3/2002 |
| EP | 1 204 146 | 5/2002 |
| EP | 1 204 147 | 5/2002 |
| EP | 1 209 747 | 5/2002 |
| EP | 0 744 772 | 8/2002 |
| EP | 1 233 454 | 8/2002 |
| EP | 0 725 402 | 9/2002 |
| EP | 1 237 193 | 9/2002 |
| EP | 1 241 708 | 9/2002 |
| EP | 1 253 634 | 10/2002 |
| EP | 0 844 671 | 11/2002 |
| EP | 1 280 205 | 1/2003 |
| EP | 1 288 955 | 3/2003 |
| FR | 2 197 494 | 3/1974 |
| GB | 1 414 228 | 11/1975 |
| JP | H04-176163 A | 6/1922 |
| JP | S62-007149 A | 1/1987 |
| JP | S62-272561 | 11/1987 |
| JP | 02-294076 | 12/1990 |
| JP | 03-171768 | 7/1991 |
| JP | 05-347419 | 12/1993 |
| JP | 08-213624 | 8/1996 |
| JP | H08-213624 A | 8/1996 |
| JP | 08-274277 | 10/1996 |
| JP | H08-316337 A | 11/1996 |
| JP | 09-046688 | 2/1997 |
| JP | 09-082912 | 3/1997 |
| JP | 10-242470 | 9/1998 |
| JP | 11-087649 | 3/1999 |
| JP | 2000-247735 A | 8/2000 |
| JP | 12-274221 A | 9/2000 |
| JP | 12-389106 A | 12/2000 |
| JP | 13-180633 A | 6/2001 |
| JP | 2002-009081 | 1/2002 |
| JP | 2002-083945 | 3/2002 |
| JP | 2002-094027 | 3/2002 |
| JP | 2002-176154 | 6/2002 |
| JP | 2002-246571 | 8/2002 |
| JP | 2002-329795 | 11/2002 |
| JP | 2002-343886 | 11/2002 |
| JP | 2002-353080 | 12/2002 |
| JP | 2003-031693 | 1/2003 |
| JP | 2003-68877 A | 3/2003 |
| JP | 2003-086712 | 3/2003 |
| JP | 2003-100641 | 4/2003 |
| JP | 2003-100900 | 4/2003 |
| JP | 2003-132682 | 5/2003 |
| JP | 2003-203967 | 7/2003 |
| JP | 2003-243528 | 8/2003 |
| JP | 2004-335553 | 11/2004 |
| WO | WO 01/24268 | 4/2001 |
| WO | WO 2005/008778 | 1/2005 |

OTHER PUBLICATIONS

Arimoto, A High-Density Scalable Twin Transistor RAM (TTRAM) With Verify Control for SOI Platform Memory IPs, Nov. 2007, Solid-State Circuits.

Asian Technology Information Program (ATIP) Scoops™, "Novel Capacitorless 1T-DRAM From Single-Gate PD-SOI to Double-Gate FinDRAM", May 9, 2005, 9 pages.

Assaderaghi et al., "A Dynamic Threshold Voltage MOSFET (DTMOS) for Ultra-Low Voltage Operation", IEEE IEDM, 1994, pp. 809-812.

Assaderaghi et al., "A Dynamic Threshold Voltage MOSFET (DTMOS) for Very Low Voltage Operation", IEEE Electron Device Letters, vol. 15, No. 12, Dec. 1994, pp. 510-512.

Assaderaghi et al., "A Novel Silicon-On-Insulator (SOI) MOSFET for Ultra Low Voltage Operation", 1994 IEEE Symposium on Low Power Electronics, pp. 58-59.

Assaderaghi et al., "Dynamic Threshold-Voltage MOSFET (DTMOS) for Ultra-Low Voltage VLSI", IEEE Transactions on Electron Devices, vol. 44, No. 3, Mar. 1997, pp. 414-422.

Assaderaghi et al., "High-Field Transport of Inversion-Layer Electrons and Holes Including Velocity Overshoot", IEEE Transactions on Electron Devices, vol. 44, No. 4, Apr. 1997, pp. 664-671.

Avci, Floating Body Cell (FBC) Memory for 16-nm Technology with Low Variation on Thin Silicon and 10-nm BOX, Oct. 2008, SOI Conference.

Bae, Evaluation of 1T RAM using Various Operation Methods with SOONO (Silicon-On-ONO) device, Dec. 2008, IEDM.

Ban et al., Integration of Back-Gate Doping for 15-nm Node Floating Body Cell (FBC) Memory, Components Research, Process Technology Modeling, presented in the 2010 VLSI Symposium on Jun. 17, 2010.

Ban, A Scaled Floating Body Cell (FBC) Memory with High-k+Metal Gate on Thin-Silicon and Thin-BOX for 16-nm Technology Node and Beyond, Jun. 2008, VLSI Symposium.

Ban, Ibrahim, et al., "Floating Body Cell with Independently-Controlled Double Gates for High Density Memory," Electron Devices Meeting, 2006. IEDM '06, International, IEEE, Dec. 11-13, 2006.

Bawedin, Maryline, et al., A Capacitorless 1T Dram on SOI Based on Dynamic Coupling and Double-Gate Operation, IEEE Electron Device Letters, vol. 29, No. 7, Jul. 2008.

Blagojevic et al., Capacitorless 1T DRAM Sensing Scheme Automatice Reference Generation, 2006, IEEE J.Solid State Circuits.

Blalock, T., "A High-Speed Clamped Bit-Line Current-Mode Sense Amplifier", IEEE Journal of Solid-State Circuits, vol. 26, No. 4, Apr. 1991, pp. 542-548.

Butt, Scaling Limits of Double Gate and Surround Gate Z-RAM Cells, 2007, IEEE Trans. On El. Dev.

Chan et al., "Effects of Floating Body on Double Polysilicon Partially Depleted SOI Nonvolatile Memory Cell", IEEE Electron Device Letters, vol. 24, No. 2, Feb. 2003, pp. 75-77.

Chan, et al., "SOI MOSFET Design for All-Dimensional Scaling with Short Channel, Narrow Width and Ultra-thin Films", IEEE IEDM, 1995, pp. 631-634.

Chi et al., "Programming and Erase with Floating-Body for High Density Low Voltage Flash EEPROM Fabricated on SOI Wafers", Proceedings 1995 IEEE International SOI Conference, Oct. 1995, pp. 129-130.

Cho et al., "Novel DRAM Cell with Amplified Capacitor for Embedded Application", IEEE, Jun. 2009.

Cho, A novel capacitor-less DRAM cell using Thin Capacitively-Coupled Thyristor (TCCT), 2005, IEDM.

Choi et al., Current Flow Mechanism in Schottky-Barrier MOSFET and Application to the 1T-DRAM, 2008, SSDM.

Choi, High Speed Flash Memory and 1T-DRAM on Dopant Segregated Schottky Barrier (DSSB) FinFET SONOS Device for Multifunctional SoC Applications, Dec. 2008, IEDM.

Clarke, Junctionless Transistors Could Simply Chip Making, Say Researchers, EE Times, Feb. 2010, www.eetimes.com/showArticle.jhtml?articleID=223100050.

Colinge, J.P., "An SOI voltage-controlled bipolar-MOS device", IEEE Transactions on Electron Devices, vol. ED-34, No. 4, Apr. 1987, pp. 845-849.

Colinge, Nanowire Transistors Without Junctions, Nature NanoTechnology, vol. 5, 2010, pp. 225-229.

Collaert et al., Optimizing the Readout Bias for the Capacitorless 1T Bulk FinFET RAM Cell, 2009, IEEE EDL.

Collaert, Comparison of scaled floating body RAM architectures, Oct. 2008, SOI Conference.

Ershov, Optimization of Substrate Doping for Back-Gate Control in SOI T-RAM Memory Technology, 2005, SOI Conference.

Ertosun et al., A Highly Scalable Capacitorless Double Gate Quantum Well Single Transistor DRAM: 1T-QW DRAM, 2008, IEEE EDL.

Fazan et al., "A Simple 1-Transistor Capacitor-Less Memory Cell for High Performance Embedded DRAMs", IEEE 2002 Custom Integrated Circuits Conference, Jun. 2002, pp. 99-102.

Fazan, A Highly Manufacturable Capacitor-less 1T-DRAM Concept, 2002, SPIE.

Fazan, et al., "Capacitor-Less 1—Transistor DRAM", 2002 IEEE International SOI Conference, Oct. 2002, pp. 10-13.

Fazan, P., "MOSFET Design Simplifies DRAM", EE Times, May 14, 2002 (3 pages).

Fisch, Beffa, Bassin, Soft Error Performance of Z-RAM Floating Body Memory, 2006, SOI Conference.

Fisch, Carman, Customizing SOI Floating Body Memory Architecture for System Performance and Lower Cost, 2006, SAME.

Fisch, Z-RAM® Ultra-Dense Memory for 90nm and Below, 2006, Hot Chips.

Fossum et al., New Insights on Capacitorless Floating Body DRAM Cells, 2007, IEEE EDL.

Fujita, Array Architecture of Floating Body Cell (FBC) with Quasi-Shielded Open Bit Line Scheme for sub-40nm Node, 2008, SOI Conference.

Furuhashi, Scaling Scenario of Floating Body Cell (FBC) Suppressing Vth Variation Due to Random Dopant Fluctuation, Dec. 2008, SOI Conference.

Furuyama et al., "An Experimental 2-bit/Cell Storage DRAM for Macrocell or Memory-on-Logic Application", IEEE Journal of Solid-State Circuits, vol. 24, No. 2, Apr. 1989, pp. 388-393.

Giffard et al., "Dynamic Effects in SOI MOSFET's", IEEE, 1991, pp. 160-161.

Gupta et al., Spice Modeling of Self Sustained Operation (SSO) to Program Sub-90nm Floating Body Cells, Oct. 2009, Conf on Simulation of Semiconductor Processes & Devices.

Han et al., Bulk FinFET Unified-RAM (URAM) Cell for Multifunctioning NVM and Capacitorless 1T-DRAM, 2008, IEEE EDL.

Han et al., Partially Depleted SONOS FinFET for Unified RAM (URAM) Unified Function for High-Speed 1T DRAM and Nonvolatile Memory, 2008, IEEE EDL.

Han, Energy Band Engineered Unified-RAM (URAM) for Multi-Functioning 1T-DRAM and NVM, Dec. 2008, IEDM.

Han, Parasitic BJT Read Method for High-Performance Capacitorless 1T-DRAM Mode in Unified RAM, Oct. 2009, IEEE EDL.

Hara, Y., "Toshiba's DRAM Cell Piggybacks on SOI Wafer", EE Times, Jun. 2003.

Hu, C., "SOI (Silicon-on-Insulator) for High Speed Ultra Large Scale Integration", Jpn. J. Appl. Phys. vol. 33 (1994) pp. 365-369, Part 1, No. 1B, Jan. 1994.

Idei et al., "Soft-Error Characteristics in Bipolar Memory Cells with Small Critical Charge", IEEE Transactions on Electron Devices, vol. 38, No. 11, Nov. 1991, pp. 2465-2471.

Ikeda et al., "3-Dimensional Simulation of Turn-off Current in Partially Depleted SOI MOSFETs", IEIC Technical Report, Institute of Electronics, Information and Communication Engineers, 1998, vol. 97, No. 557 (SDM97 186-198), pp. 27-34.

Inoh et al., "FBC (Floating Body Cell) for Embedded DRAM on SOI", 2003 Symposium on VLSI Circuits Digest of Technical Papers, Jun. 2003 (2 pages).

Iyer et al., "SOI MOSFET on Low Cost SPIMOX Substrate", IEEE IEDM, Sep. 1998, pp. 1001-1004.

Jang et al., Highly scalable Z-RAM with remarkably long data retention for DRAM application, Jun. 2009, VLSI.

Jeong et al., "A Capacitor-less 1T DRAM Cell Based on a Surrounding Gate MOSFET with Vertical Channel", Technology Development Team, Technology Development Team, Samsung Electronics Co., Ltd., May 2007.

Jeong et al., "A New Capacitorless 1T DRAm Cell: Surrounding Gate MOSFET with Vertical Channel (SGVC Cell)", IEEE Transactions on Nanotechnology, vol. 6, No. 3, May 2007.

Jeong et al., "Capacitorless DRAM Cell with Highly Scalable Surrounding Gate Structure", Extended Abstracts of the 2006 International Conference on Solid State Devices and Materials, pp. 574-575, Yokohama (2006).

Jeong et al., "Capacitorless Dynamic Random Access Memory Cell with Highly Scalable Surrounding Gate Structure", Japanese Journal of Applied Physics, vol. 46, No. 4B, pp. 2143-2147 (2007).

Kedzierski, J.; "Design Analysis of Thin-Body Silicide Source/Drain Devices", 2001 IEEE International SOI Conference, Oct. 2001, pp. 21-22.

Kim et al., "Chip Level Reliability on SOI Embedded Memory", Proceedings 1998 IEEE International SOI Conference, Oct. 1998, pp. 135-139.

Kuo et al., "A Capacitorless Double-Gate DRAM Cell Design for High Density Applications", IEEE IEDM, Feb. 2002, pp. 843-846.

Kuo et al., "A Capacitorless Double-Gate DRAM Cell", IEEE Electron Device Letters, vol. 23, No. 6, Jun. 2002, pp. 345-347.

Kuo et al., A Capacitorless Double Gate DRAM Technology for Sub 100 nm Embedded and Stand Alone Memory Applications, 2003, IEEE Trans. On El. Dev.

Kwon et al., "A Highly Scalable 4F2 DRAm Cell Utilizing a Doubly Gated Vertical Channel", Extended Abstracts of the 2009 International Conference on Solid State Devices and Materials, UC Berkley, pp. 142-143 Sendai (2009).

Lee et al., "A Novel Pattern Transfer Process for Bonded SOI Giga-bit DRAMs", Proceedings 1996 IEEE International SOI Conference, Oct. 1996, pp. 114-115.

Leiss et al., dRAM Design Using the Taper-Isolated Dynamic RAM Cell, IEEE Transactions on Electron Devices, vol. ED-29, No. 4, Apr. 1982, pp. 707-714.

Lin et al., "Opposite Side Floating Gate SOI Flash Memory Cell", IEEE, Mar. 2000, pp. 12-15.

Liu et al., Surface Generation-Recombination Processes of Gate and STI Oxide Interfaces Responsible for Junction Leakage on SOI, Sep. 2009, ECS Transactions, vol. 25.

Liu, Surface Recombination-Generation Processes of Gate, STI and Buried Oxide Interfaces, Responsible for Junction Leakage, ICSI, May 19, 2009.

Lončar et al., "One of Application of SOI Memory Cell—Memory Array", IEEE Proc. 22nd International Conference on Microelectronics (MIEL 2000), vol. 2, NIŠ, Serbia, May 14-17, 2000, pp. 455-458.

Lu et al., A Novel Two—Transistor Floating Body/Gate Cell for Low Power Nanoscale Embedded DRAM, 2008, IEEE Trans. On El. Dev.

Ma, et al., "Hot-Carrier Effects in Thin-Film Fully Depleted SOI MOSFET's", IEEE Electron Device Letters, vol. 15, No. 6, Jun. 1994, pp. 218-220.

Malhi et al., "Characteristics and Three-Dimensional Integration of MOSFET's in Small-Grain LPCVD Polycrystalline Silicon", IEEE Transactions on Electron Devices, vol. ED-32, No. 2, Feb. 1985, pp. 258-281.

Malinge, An 8Mbit DRAM Design Using a 1TBulk Cell, 2005, VLSI Circuits.

Mandelman et al, "Floating-Body Concerns for SOI Dynamic Random Access Memory (DRAM)", Proceedings 1996 IEEE International SOI Conference, Oct. 1996, pp. 136-137.

Matsuoka et al., FBC Potential of 6F2 Single Cell Operation in Multi Gbit Memories Confirmed by a Newly Developed Method for Measuring Signal Sense Margin, 2007, IEDM.

Minami, A Floating Body Cell (FBC) fully Compatible with 90nm CMOS Technology(CMOS IV) for 128Mb SOI DRAM, 2005, IEDM.

Mohapatra et al., Effect of Source/Drain Asymmetry on the Performance of Z-RAMÒ Devices, Oct. 2009, SOI conference.

Morishita, A Capacitorless Twin-Transistor Random Access Memory (TTRAM) on SOI, 2005, CICC.

Morishita, F. et al., "A Configurable Enhanced TTRAM Macro for System-Level Power Management Unified Memory", IEEE Journal of Solid-State Circuits, vol. 42, No. 4, pp. 853, Apr. 2007.

Morishita, F., et al., "A 312-MHz 16-Mb Random-Cycle Embedded DRAM Macro With a Power-Down Data Retention Mode for Mobile Applications", J. Solid-State Circuits, vol. 40, No. 1, pp. 204-212, 2005.

Morishita, F., et al., "Dynamic floating body control SOI CMOS for power managed multimedia ULSIs", Proc. CICC, pp. 263-266, 1997.

Morishita, F., et al., "Leakage Mechanism due to Floating Body and Countermeasure on Dynamic Retention Mode of SOI-DRAM", Symposium on VLSI Technology Digest of Technical Papers, pp. 141-142, 1995.

Nagoga, Studying of Hot Carrier Effect in Floating Body Soi Mosfets by the Transient Charge Pumping Technique, Switzerland 2003.

Nayfeh, A Leakage Current Model for SOI based Floating Body Memory that Includes the Poole-Frenkel Effect, 2008, SOI Conference.

Nemati, A Novel High Density, Low Voltage SRAM Cell with a Vertical NDR Device, 1998, VLSI Tech. Symp.

Nemati, A Novel Thyristor-based SRAM Cell (T-RAM) for High-Speed, Low-Voltage, Giga-scale Memories, 1999, IEDM Conference.

Nemati, Embedded Volatile Memories-Embedded Tutorial: The New Memory Revolution, New Drives Circuits and Systems, ICCAD 2008, Nov. 2008.

Nemati, Fully Planar 0.562 µm2 T-RAM Cell in a 130nm SOI CMOS Logic Technology for High-Density High-Performance SRAMs, 2004, IEDM.

Nemati, The New Memory Revolution. New Devices, Circuits and Systems, 2008, ICCAD.

Nemati, Thyristor RAM (T-RAM): A High-Speed High-Density Embedded Memory Technology for Nano-scale CMOS, 2007, Hot Chips.

Nemati, Thyristor-RAM: A Novel Embedded Memory Technology that Outperforms Embedded S RAM/DRAM, 2008, Linley Tech Tour.

Nishiguchi et al., Long Retention of Gain-Cell Dynamic Random Access Memory with Undoped Memory Node, 2007, IEEE EDL.

Oh, Floating Body DRAM Characteristics of Silicon-On-Ono (SOONO) Devices for System-on-Chip (SoC) Applications, 2007, VLSI Symposium.

Ohno et al., "Suppression of Parasitic Bipolar Action in Ultra-Thin-Film Fully-Depleted CMOS/SIMOX Devices by Ar-Ion Implantation into Source/Drain Regions", IEEE Transactions on Electron Devices, vol. 45, No. 5, May 1998, pp. 1071-1076.

Ohsawa et al., "A Memory Using One-Transistor Gain Cell on SOI (FBC) with Performance Suitable for Embedded DRAM's", 2003 Symposium on VLSI Circuits Digest of Technical Papers, Jun. 2003 (4 pages).

Ohsawa et al., "Memory Design Using a One-Transistor Gain Cell on SOI", IEEE Journal of Solid-State Circuits, vol. 37, No. 11, Nov. 2002, pp. 1510-1522.

Ohsawa, A 128Mb Floating Body RAM (FBRAM) on SOI with a Multi-Averaging Scheme of Dummy Cell, 2006 Symposium of VLSI Circuits Digest of Tech Papers, (2006).

Ohsawa, An 18.5ns 128Mb SOI DRAM with a Floating Body Cell, 2005, ISSCC.

Ohsawa, Autonomous Refresh of Floating Body Cell (FBC), Dec. 2008, IEDM.

Ohsawa, Design of a 128-Mb SOI DRAM Using the Floating Body Cell (FBC), Jan. 2006, Solid-State Circuits.

Okhonin, A Capacitor-Less 1T-DRAM Cell, Feb. 2002, Electron Device Letters.

Okhonin, A SOI Capacitor-less 1T-DRAM Concept, 2001, SOI Conference.

Okhonin, Charge Pumping Effects in Partially Depleted SOI MOSFETs, 2003, SOI Conference.

Okhonin, New characterization techniques for SOI and related devices, 2003, ECCTD.

Okhonin, New Generation of Z-RAM, 2007, IEDM.

Okhonin, Principles of Transient Charge Pumping on Partially Depleted SOI MOSFETs, May 2002, Electron Device Letters.

Okhonin, Transient Charge Pumping for Partially and Fully Depleted SOI MOSFETs, 2002, SOI Conference.

Okhonin, Transient effects in PD SOI MOSFETs and potential DRAM applications, 2002, Solid-State Electronics.

Okhonin, Ultra-scaled Z-RAM cell, 2008, SOI Conference.

Okhonin, Z-RAM® (Limits of DRAM), 2009, ESSDERC.

Padilla, Alvaro, et al., "Feedback FET: A Novel Transistor Exhibiting Steep Switching Behavior at Low Bias Voltages," Electron Devices Meeting, 2008. IEDM 2008. IEEE International, Dec. 5-17, 2008.

Park, Fully Depleted Double-Gate 1T-DRAM Cell with NVM Function for High Performance and High Density Embedded DRAM, 2009, IMW.

Pelella et al., "Low-Voltage Transient Bipolar Effect Induced by Dynamic Floating-Body Charging in PD/SOI MOSFETs", Final Camera Ready Art, SOI Conference, Oct. 1995, 2 pages.

Portmann et al., "A SOI Current Memory for Analog Signal Processing at High Temperature", 1999 IEEE International SOI Conference, Oct. 1999, pp. 18-19.

Puget et al., 1T Bulk eDRAM using GIDL Current for High Speed and Low Power applications, 2008, SSDM.

Puget et al., Quantum effects influence on thin silicon film capacitor-less DRAM performance, 2006, SOI Conference.

Puget, FDSOI Floating Body Cell eDRAM Using Gate-Induced Drain-Leakage (GIDL) Write Current for High Speed and Low Power Applications, 2009, IMW.

Ranica et al., 1T-Bulk DRAM cell with improved performances: the way to scaling, 2005, ICMTD.

Ranica, A capacitor-less DRAM cell on 75nm gate length, 16nm thin Fully Depleted SOI device for high density embedded memories, 2004, IEDM.

Ranica, A One Transistor Cell on Bulk Substrate (1T-Bulk) for Low-Cost and High Density eDRAM, 2004, VLSI Symposium.

Rodder et al., "Silicon-On-Insulator Bipolar Transistors", IEEE Electron Device Letters, vol. EDL-4, No. 6, Jun. 1983, pp. 193-195.

Rodriguez, Noel, et al., A-RAM Novel Capacitor-less Dram Memory, SOI Conference, 2009 IEEE International, Oct. 5-8, 2009 pp. 1-2.

Roy, Thyristor-Based Volatile Memory in Nano-Scale CMOS, 2006, ISSCC.

Salling et al., Reliability of Thyristor Based Memory Cells, 2009, IRPS.

Sasaki et al., Charge Pumping in SOS-MOS Transistors, 1981, IEEE Trans. On El. Dev.

Sasaki et al., Charge Pumping SOS-MOS Transistor Memory, 1978, IEDM.

Schloesser et al., "A 6F2 Buried Wordline DRAM Cell for 40nm and Beyond", IEEE, Qimonda Dresden GmbH & Co., pp. 809-812 (2008).

Shino et al., Floating Body RAM technology and its scalability to 32 nm node and beyond, 2006, IEDM.

Shino et al., Operation Voltage Dependence of Memory Cell Characteristics in Fully Depleted FBC, 2005, IEEE Trans. On El. Dev.

Shino, Fully-Depleted FBC (Floating Body Cell) with Enlarged Signal Window and Excellent Logic Process Compatibility, 2004, IEDM.

Shino, Highly Scalable FBC (Floating Body Cell) with 25nm BOX Structure for Embedded DRAM Applications, 2004, VLSI Symposium.

Sim et al., "Source-Bias Dependent Charge Accumulation in P+—Poly Gate SOI Dynamic Random Access Memory Cell Transistors", Jpn. J. Appl. Phys. vol. 37 (1998) pp. 1260-1263, Part 1, No. 3B, Mar. 1998.

Singh, A 2ns-Read-Latency 4Mb Embedded Floating-Body Memory Macro in 45nm SOI Technology, Feb. 2009, ISSCC.

Sinha et al., "In-Depth Analysis of Opposite Channel Based Charge Injection in SOI MOSFETs and Related Defect Creation and Annihilation", Elsevier Science, Microelectronic Engineering 28, 1995, pp. 383-386.

Song, 55 nm Capacitor-less 1T DRAM Cell Transistor with Non-Overlap Structure, Dec. 2008, IEDM.

Stanojevic et al., "Design of a SOI Memory Cell", IEEE Proc. 21st International Conference on Microelectronics (MIEL '97), vol. 1, NIS, Yugoslavia, Sep. 14-17, 1997, pp. 297-300.

Su et al., "Studying the Impact of Gate Tunneling on Dynamic Behaviors of Partially-Depleted SOI CMOS Using BSIMPD", IEEE Proceedings of the International Symposium on Quality Electronic Design (ISQED '02), Apr. 2002 (5 pages).

Suma et al., "An SOI-DRAM with Wide Operating Voltage Range by CMOS/SIMOX Technology", 1994 IEEE International Solid-State Circuits Conference, pp. 138-139.

Tack et al., "The Multi-Stable Behaviour of SOI-NMOS Transistors at Low Temperatures", Proc. 1988 SOS/SOI Technology Workshop (Sea Palms Resort, St. Simons Island, GA, Oct. 1988), p. 78.

Tack et al., "The Multistable Charge Controlled Memory Effect in SOI Transistors at Low Temperatures", IEEE Workshop on Low Temperature Electronics, Aug. 7-8, 1989, University of Vermont, Burlington, pp. 137-141.

Tack et al., "The Multistable Charge-Controlled Memory Effect in SOI MOS Transistors at Low Temperatures", IEEE Transactions on Electron Devices, vol. 37, No. 5, May 1990, pp. 1373-1382.

Tack, et al., "An Analytical Model for the Misis Structure in SOI MOS Devices", Solid-State Electronics vol. 33, No. 3, 1990, pp. 357-364.

Tanaka et al., "Scalability Study on a Capacitorless 1T-DRAM: From Single-gate PD-SOI to Double-gate FINDRAM", 2004 IEEE, 4 pages.

Tang, Poren, Highly Scalable Capacitorless DRAM Cell on Thin-Body with Band-gap Engineered Source and Drain, Extended Abstracts of the 2009 ICSSDM, Sendai, 2009, pp. 144-145.

Terauchi et al., "Analysis of Floating-Body-Induced Leakage Current in 0.15 μm SOI DRAM", Proceedings 1996 IEEE International SOI Conference, Oct. 1996, pp. 138-139.

Thomas et al., "An SOI 4 Transistors Self-Refresh Ultra-Low-Voltage Memory Cell", IEEE, Mar. 2003, pp. 401-404.

Tomishima, et al., "A Long Data Retention SOI DRAM with the Body Refresh Function", IEICE Trans. Electron., vol. E80—C, No. 7, Jul. 1997, pp. 899-904.

Tsaur et al., "Fully Isolated Lateral Bipolar-MOS Transistors Fabricated in Zone-Melting-Recrystallized Si Films on SiO2", IEEE Electron Device Letters, vol. EDL-4, No. 8, Aug. 1983, pp. 269-271.

Tu, et al., "Simulation of Floating Body Effect in SOI Circuits Using BSIM3SOI", Proceedings of Technical Papers (IEEE Cat No. 97TH8303), Jun. 1997, pp. 339-342.

Villaret et al., "Mechanisms of Charge Modulation in the Floating Body of Triple-Well nMOSFET Capacitor-less DRAMs", Proceedings of the INFOS 2003, Insulating Films on Semiconductors, 13th Bi-annual Conference, Jun. 18-20, 2003, Barcelona (Spain), (4 pages).

Villaret et al., "Triple-Well nMOSFET Evaluated as a Capacitor-Less DRAM Cell for Nanoscale Low-Cost & High Density Applications", Handout at Proceedings of 2003 Silicon Nanoelectronics Workshop, Jun. 8-9, 2003, Kyoto, Japan (2 pages).

Villaret et al., Further Insight into the Physics and Modeling of Floating Body Capacitorless DRAMs, 2005, IEEE Trans. On El. Dev.

Wang et al., A Novel 4.5F2 Capacitorless Semiconductor Memory Device, 2008, IEEE EDL.

Wann et al., "A Capacitorless DRAM Cell on SOI Substrate", IEEE IEDM, 1993, pp. 635-638.

Wann et al., "High-Endurance Ultra-Thin Tunnel Oxide in MONOS Device Structure for Dynamic Memory Application", IEEE Electron Device Letters, vol. 16, No. 11, Nov. 1995, pp. 491-493.

Wei, A., "Measurement of Transient Effects in SOI DRAM/SRAM Access Transistors", IEEE Electron Device Letters, vol. 17, No. 5, May 1996, pp. 193-195.

Wouters, et al., "Characterization of Front and Back Si-SiO2 Interfaces in Thick- and Thin-Film Silicon-on-Insulator MOS Structures by the Charge-Pumping Technique", IEEE Transactions on Electron Devices, vol. 36, No. 9, Sep. 1989, pp. 1746-1750.

Wu, Dake, "Performance Improvement of the Capacitorless DRAM Cell with Quasi-SOI Structure Based on Bulk Substrate," Extended Abstracts of the 2009 ICSSDM, Sendai, 2009, pp. 146-147.

Yamanaka et al., "Advanced TFT SRAM Cell Technology Using a Phase-Shift Lithography", IEEE Transactions on Electron Devices, vol. 42, No. 7, Jul. 1995, pp. 1305-1313.

Yamauchi et al., "High-Performance Embedded SOI DRAM Architecture for the Low-Power Supply", IEEE Journal of Solid-State Circuits, vol. 35, No. 8, Aug. 2000, pp. 1169-1178.

Yamawaki, M., "Embedded DRAM Process Technology", Proceedings of the Symposium on Semiconductors and Integrated Circuits Technology, 1998, vol. 55, pp. 38-43.

Yang, Optimization of Nanoscale Thyristors on SOI for High-Performance High-Density Memories, 2006, SOI Conference.

Yoshida et al., "A Design of a Capacitorless 1-T-DRAM Cell Using Gate-induced Drain Leakage (GIDL) Current for Low-Power and High-speed Embedded Memory", 2003 IEEE, 4 pages.

Yoshida et al., "A Study of High Scalable DG-FinDRAM", IEEE Electron Device Letters, vol. 26, No. 9, Sep. 2005, pp. 655-657.

Yoshida et al., A Capacitorless 1T-DRAM Technology Using GIDL Current for Low Power and High Speed Embedded Memory, 2006, IEEE Trans. On El. Dev.

Yu et al., Hot-Carrier Effect in Ultra-Thin-Film (UTF) Fully-Depleted SOI MOSFET's, 54th Annual Device Research Conference Digest (Cat. No. 96TH8193), Jun. 1996, pp. 22-23.

Yu et al., "Hot-Carrier-Induced Degradation in Ultra-Thin-Film Fully-Depleted SOI MOSFETs", Solid-State Electronics, vol. 39, No. 12, 1996, pp. 1791-1794.

Yu et al., "Interface Characterization of Fully-Depleted SOI MOSFET by a Subthreshold I-V Method", Proceedings 1994 IEEE International SOI Conference, Oct. 1994, pp. 63-64.

Yun et al., Analysis of Sensing Margin in SOONO Device for the Capacitor-less RAM Applications, 2007, SOI Conference.

Zhou, Physical Insights on BJT-Based 1T DRAM Cells, IEEE Electron Device Letters, vol. 30, No. 5, May 2009.

"A 30-ns 64-MB DRAM with Built-in Self-Test and Self-Repair Function," Tanabe et al., IEEE Journal of Sold-Sate Circuits, vol. 27, No. 11, Nov. 1992, pp. 1525-1533.

\* cited by examiner

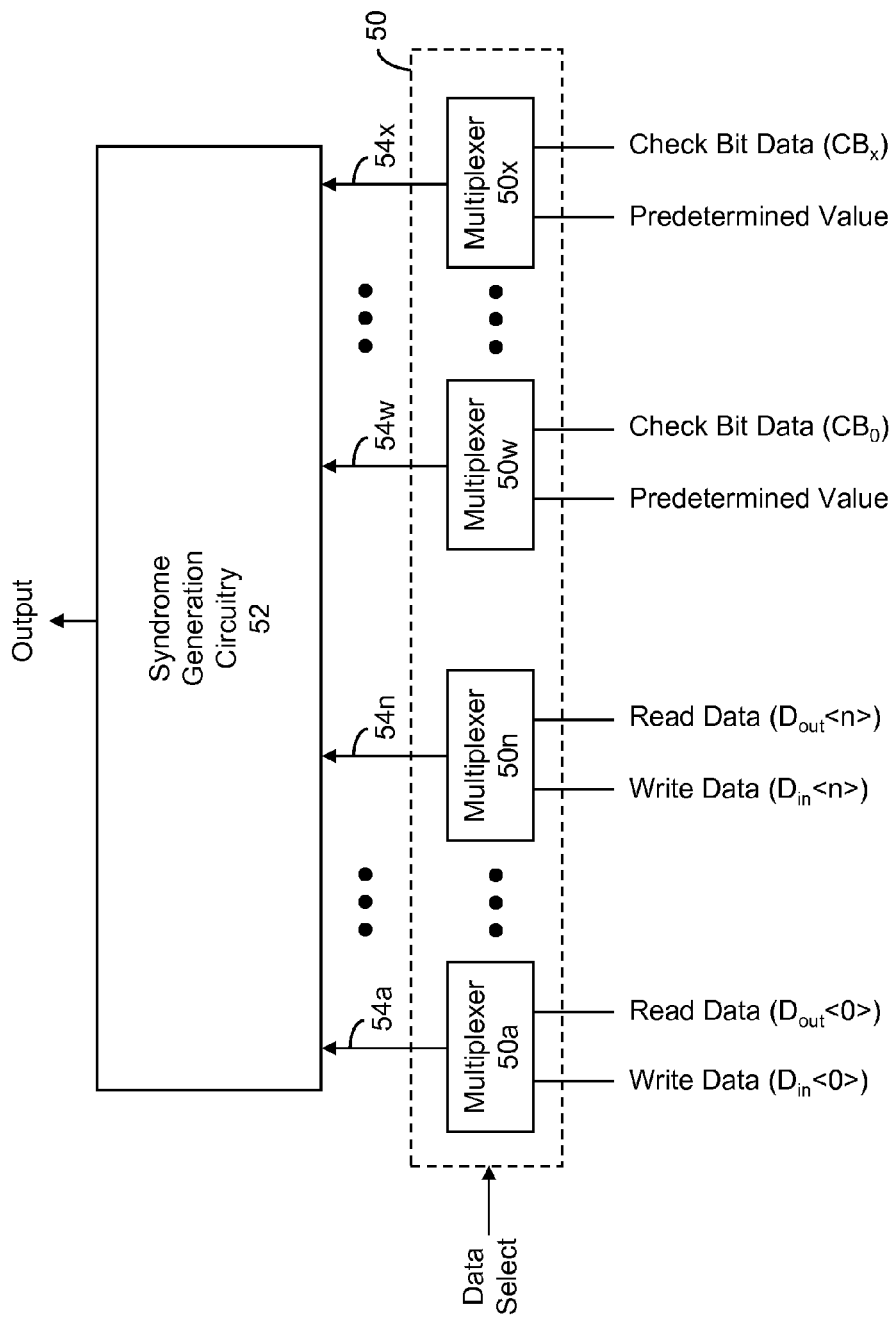

INTEGRATED CIRCUIT HAVING MEMORY ARRAY INCLUDING ECC AND COLUMN REDUNDANCY AND METHOD OF OPERATING SAME

CROSS REFERENCE TO RELATED APPLICATIONS

This patent application is a continuation of U.S. patent application Ser. No. 11/821,469, filed Jun. 22, 2007, now U.S. Pat. No. 8,069,377, which claims priority to U.S. Provisional Patent Application No. 60/816,416, filed Jun. 26, 2006, each of which is hereby incorporated by reference herein in its entirety.

BACKGROUND

In one aspect, the present inventions described and illustrated herein relate to an integrated circuit device having a memory cell array including error checking and correcting (ECC) circuitry and/or column redundancy, and techniques for programming, configuring, controlling and/or operating such device. More particularly, in one aspect, the present inventions relate to an integrated circuit having random access memory ("RAM") array having a plurality of memory cells (for example, memory cells having an electrically floating body in which an electrical charge is stored) arranged in a matrix of rows and columns wherein the integrated circuit includes an ECC architecture and/or a column redundancy architecture including at least one redundant column to substitute or replace a column of memory cells having at least one defective memory cell.

Briefly, with reference to FIG. 1A, memory cell array 10 typically includes a plurality of memory cells 12 arranged in a matrix of rows 14 (each typically having a common word line 16) and columns 18. A row address decoder 20 enables one or more rows to be read by sensing circuitry 22 (for example, a plurality of sense amplifiers). A column decoder 24, in response to an address, selects one or more of the outputs of the sensing circuitry 22.

One technique to improve the reliability of the data stored and/or output by dense memories is to employ ECC techniques. ECC techniques (for example, techniques to correct or reduce the impact of alpha particle induced soft error rate and/or errors caused by random defects in memory structures due to, for example, various complex fabrication processes) generally require the implementation of exclusive OR gates ("XOR") to calculate the parity of the ECC word. A longer ECC word requires the calculation of parity of more bits and hence requires "wider" XOR gates. Conventional schemes for parity calculation using wide XOR gates must address the challenges associated with wiring the various bits (sometimes from across the width of memory array 10) to the inputs of XOR gates. Notably, conventional techniques tend to employ a XOR tree in the read path (Read XOR Tree) and write path (Write XOR Tree). (See, FIG. 1B).

In addition, conventional implementations of the Single Error Correction (SEC) scheme using Hamming code often have a critical path for speed that begins from the bits read from the memory array (data and check bits), through the wide XOR gates to calculate the "syndrome" vector, which is then decoded to identify the position of the erroneous bit in the "ECC word". This information is used to correct the error during the read operation. During the memory write operation, wide XOR gates are used to calculate the parity and produce the "check bits" for the ECC word, which are then written into the array along with the data.

In order to improve, enhance and/or maintain a predetermined manufacturing yield of a memory cell array and/or device, one or more redundant columns 18r are often incorporated into memory array 10 to logically "replace" one or more columns 18 having one or more defective memory cells 12 and/or sense circuitry 22.

In one conventional technique, column redundancy is implemented by including a redundant column address decoder 24r which is programmed or mapped to logically replace a defective column (i.e., a column of memory cells having one or more defective memory cells and/or defective sense circuitry 22) with spare, replacement, redundant or another column 18r of memory cells 12r in memory array 10 (i.e., redundant column 18r of memory cells 12r). The individual address comparators (not illustrated) of redundant column decoder 20r are programmed to "enable" spare or redundant data sense circuitry 22r when the "applied" address matches the address of the defective column (which is fixed/stored in redundant column address decoder 24r). In this regard, the address of the defective column 18 is programmed into address comparators of redundant column decoder 24r during wafer testing. In this way, the redundant column address comparators enable a spare or redundant data sense circuitry 22r to be active when a set of column address signals match the address of a defective column 18 which is programmed into redundant column address decoder 24r.

One conventional redundancy technique employs a set of fuses to program or configure redundant column decoder 24r. In this regard, spare or redundant columns are programmed by selectively "blowing" fuses (not illustrated) within redundant column decoder 24r to "match" or correspond to the address of the columns having defective memory cells. Such fuses are often programmed prior to packaging, during the wafer testing stage, or immediately after packaging, during the device testing stage. In this way, spare or redundant data sense circuitry 22r (and data output path corresponding thereto) is enabled when the address matches the address programmed into redundant column decoder 24r.

A multiplexer may be employed in the data output path that responsively selects between the data from normal column and a spare column. Under normal operation, the multiplexers select the data from normal column. The multiplexer associated with the defective column may be enabled to select the data from the spare column which thereby incorporates the data from the spare or redundant column into the output path. A multiplexer may also be implemented on the write input path, where the data slated to be written into the defective column is "steered" to the spare or redundant column.

Notably, disabling circuitry may be implemented in memory array 10 to disable the data sense circuitry corresponding to the defective column when the address matches the address programmed into redundant column decoder 24r. As such, in response to a "match" between the applied column address and the address programmed in redundant column decoder 24r, normal data sense circuitry 22 (and data output path corresponding thereto) associated with the defective column is disabled and redundant data sense circuitry 22r (and data output path corresponding thereto) is enabled.

SUMMARY

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

In a first principle aspect, the present inventions are directed to an integrated circuit device (for example, logic device or discrete memory device) comprising a memory cell array including a plurality of memory cells arranged in a matrix of rows and columns, multiplexer circuitry, coupled to the memory cell array, and syndrome generation circuitry. The multiplexer circuitry includes a plurality of data multiplexers, each data multiplexer having a plurality of inputs, including (i) a first input to receive write data which is representative of data to be written into the memory cells of the memory cell array in response to a write operation, and (ii) a second input to receive read data which is representative of data read from memory cells of the memory cell array, and an associated output to responsively output data from one of the plurality of inputs. The syndrome generation circuitry is coupled to the multiplexer circuitry and generates: (i) a write data syndrome vector using the write data and (ii) a read data syndrome vector using the read data.

In one embodiment, the syndrome generation circuitry includes a plurality of XOR logic gates. The plurality of XOR logic gates may be arranged in a logic tree architecture. In one embodiment, the logic tree architecture includes first, second and third levels of XOR logic, wherein the first level of XOR logic includes inputs to receive the outputs of the plurality of data multiplexers, the second level of XOR logic includes inputs to receive the outputs of the first level of XOR logic, and the third level of XOR logic includes inputs to receive the outputs of the second level of XOR logic. In another embodiment, the logic tree architecture includes a plurality of levels of XOR logic levels, wherein an Nth level of XOR logic includes (i) inputs to receive the outputs of a preceding level of XOR logic gates and data from at least one redundant or spare column and (ii) an output that is the read data syndrome vector.

The multiplexer circuitry of this aspect of the inventions may further include a plurality of check bit multiplexers, each check bit multiplexer having a plurality of inputs, including (i) a first input to receive check bit data, and (ii) a second input to receive a predetermined data, and an associated output to responsively output data from one of the plurality of inputs. The syndrome generation circuitry may generate: (i) a write data syndrome vector using the write data and the predetermined value, and (ii) a read data syndrome vector using the read data and the check bit data. As noted above, in one embodiment, the syndrome generation circuitry includes a plurality of XOR logic gates. The plurality of XOR logic gates may be arranged in a logic tree architecture. In one embodiment, the logic tree architecture includes first, second and third levels of XOR logic, wherein the first level of XOR logic includes inputs to receive the outputs of the plurality of data multiplexers, the second level of XOR logic includes inputs to receive the outputs of the first level of XOR logic, and the third level of XOR logic includes inputs to receive the outputs of the second level of XOR logic. In another embodiment, the logic tree architecture includes a plurality of levels of XOR logic levels, wherein an Nth level of XOR logic includes (i) inputs to receive the outputs of a preceding level of XOR logic gates and data from at least one redundant or spare column and (ii) an output that is the read data syndrome vector.

The write data syndrome vector may be stored in memory as check bit data.

The integrated circuit device of this aspect of the inventions may further include address converter circuitry, coupled to the syndrome generation circuitry, to generate defective column address data, which is representative of a physical bit location of a defective column, using the read data syndrome vector. A memory, coupled to the address converter circuitry, may store the defective column address data. The memory may temporarily or permanently store the defective column address data.

In another principal aspect, the present inventions are an integrated circuit device (for example, logic device or discrete memory device) comprising a memory cell array, multiplexer circuitry, syndrome generation circuitry, address converter circuitry, and a plurality of redundancy program circuits. The memory cell array includes a plurality of memory cells arranged in a matrix of rows and columns including (i) a plurality of normal columns which is selectable via normal column address data and (ii) a redundant column which is selectable via a redundant column address data. The multiplexer circuitry of this aspect of the inventions is coupled to the memory cell array and includes a plurality of data multiplexers, each data multiplexer having a plurality of inputs, including (i) a first input to receive write data which is representative of data to be written into the memory cells of the memory cell array in response to a write operation, and (ii) a second input to receive read data which is representative of data read from memory cells of the memory cell array, and an associated output to responsively output data from one of the plurality of inputs. The syndrome generation circuitry, coupled to the multiplexer circuitry, to generate: (i) a write data syndrome vector using the write data and (ii) a read data syndrome vector using the read data. The address converter circuitry, coupled to the syndrome generation circuitry, to generate defective column address data, which is representative of a physical bit location of a defective column, using the read data syndrome vector. In addition, the plurality of redundancy program circuits are coupled to the memory array to receive the read data and spare column data, which is representative of data read from memory cells associated with the redundant column of the memory cell array, wherein each redundancy program circuit outputs (i) read data which is associated with one of a normal column or (ii) the spare column data, and wherein when one of a normal column address data corresponds to the defective column address data, the redundancy program circuit associated therewith outputs the defective column address data.

In one embodiment, each redundancy program circuit includes (1) a multiplexer having a plurality of inputs, including (i) a first input to receive read data which is associated with one of a normal column, and (ii) a second input to receive the spare column data, and an associated output to responsively output data from one of the plurality of inputs, and (2) a memory, coupled to an associated multiplexer, to store spare column control data which controls the associated multiplexer. The memory of each redundancy program circuit is coupled to the address converter circuitry and, in response to a program signal, the memory of the redundancy program circuit which is associated with the normal column that corresponds to the defective column address data stores the spare column control data. In one embodiment, the memory stores the spare column control data in response to a program signal.

The integrated circuit device of may further include a plurality of logic gates having a first input to receive an output of an associated redundancy program circuit and a second input to receive correction data wherein when the read data includes one or more errors therein, the one or more logic gates which receives read data having an error corrects the read data using the correction data. In one embodiment, each logic gate of the plurality of logic gates includes an XOR logic gate.

In one embodiment, the syndrome generation circuitry includes a plurality of XOR logic gates. The plurality of XOR logic gates may be arranged in a logic tree architecture. The logic tree architecture may include a plurality of levels of XOR logic levels, wherein an Nth level of XOR logic includes (i) inputs to receive the outputs of a preceding level of XOR logic gates and data from at least one redundant or spare column and (ii) an output that is the read data syndrome vector.

In one embodiment, the multiplexer circuitry further includes a plurality of check bit multiplexers, each check bit multiplexer having a plurality of inputs, including (i) a first input to receive check bit data, and (ii) a second input to receive a predetermined data, and an associated output to responsively output data from one of the plurality of inputs. The syndrome generation circuitry, in this embodiment, generates: (i) a write data syndrome vector using the write data and the predetermined value, and (ii) a read data syndrome vector using the read data and the check bit data.

The syndrome generation circuitry may include a plurality of XOR logic gates which is arranged in a logic tree architecture including a plurality of levels of XOR logic levels, wherein a Nth level of XOR logic includes (i) inputs to receive the outputs of a preceding level of XOR logic gates and data from at least one redundant or spare column and (ii) an output that is the read data syndrome vector.

The write data syndrome vector may be stored in memory as check bit data.

The integrated circuit device may further include a defective column address memory, coupled to the address converter circuitry, to store the defective column address data. The memory may temporarily or permanently store the defective column address data.

In yet another principal aspect, the integrated circuit device (for example, logic device or discrete memory device) comprises a memory cell array having a plurality of memory cells arranged in a matrix of rows and columns including (i) a plurality of normal columns which is selectable via normal column address data and (ii) a redundant column which is selectable via a redundant column address data. The integrated circuit device of this aspect further includes multiplexer circuitry, syndrome generation means, address converter means and redundancy program means. The multiplexer circuitry is coupled to the memory cell array and includes a plurality of data multiplexers, each data multiplexer having a plurality of inputs, including (i) a first input to receive write data which is representative of data to be written into the memory cells of the memory cell array in response to a write operation, and (ii) a second input to receive read data which is representative of data read from memory cells of the memory cell array, and an associated output to responsively output data from one of the plurality of inputs. The syndrome generation means generates: (i) a write data syndrome vector using the write data and (ii) a read data syndrome vector using the read data. The address converter means generates defective column address data, which is representative of a physical bit location of a defective column, using the read data syndrome vector. The redundancy program means outputs (i) read data which is associated with one of a normal column or (ii) the spare column data which is representative of data read from memory cells associated with the redundant column of the memory cell array.

The redundancy program means may include (1) multiplexer means for responsively outputting data from one of the (i) read data which is associated with one of a normal column and (ii) the spare column data, and (2) memory means for storing spare column control data which controls the multiplexer means. The memory means responsively stores information which is representative of the defective column address data.

The write data syndrome vector may be stored in memory means as check bit data. The write data syndrome vector may be stored in memory cells in the memory cell array.

Again, there are many inventions, and aspects of the inventions, described and illustrated herein. This Summary of the Inventions is not exhaustive of the scope of the present inventions. Indeed, this Summary of the Invention may not be reflective of or correlate to the inventions protected in this or in continuation/divisional applications hereof.

Moreover, this Summary of the Inventions is not intended to be limiting of the inventions or the claims (whether the currently presented claims or claims of a divisional/continuation application) and should not be interpreted in that manner. While certain embodiments have been described and/or outlined in this Summary of the Inventions, it should be understood that the present inventions are not limited to such embodiments, description and/or outline, nor are the claims limited in such a manner (which should also not be interpreted as being limited by the Summary of the Inventions).

Indeed, many other aspects, inventions and embodiments, which may be different from and/or similar to, the aspects, inventions and embodiments presented in this Summary, will be apparent from the description, illustrations and claims, which follow. In addition, although various features, attributes and advantages have been described in this Summary of the Inventions and/or are apparent in light thereof, it should be understood that such features, attributes and advantages are not required whether in one, some or all of the embodiments of the present inventions and, indeed, need not be present in any of the embodiments of the present inventions.

BRIEF DESCRIPTION OF THE DRAWINGS

In the course of the detailed description to follow, reference will be made to the attached drawings. These drawings show different aspects of the present inventions and, where appropriate, reference numerals illustrating like structures, components, materials and/or elements in different figures are labeled similarly. It is understood that various combinations of the structures, components, materials and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

FIG. 2 is a schematic block diagram illustration of an exemplary ECC architecture including syndrome generation circuitry and multiplexer circuitry according to an aspect of the present inventions;

FIGS. 8A-8C are schematic block diagram illustrations of exemplary devices in which the column redundancy and/or ECC architecture may be implemented wherein FIGS. 8A and 8C are logic devices (having logic circuitry and resident memory) and FIG. 8B is a memory device (having primarily of a memory array), according to certain aspects of the present inventions.

DETAILED DESCRIPTION

Figure 1A:
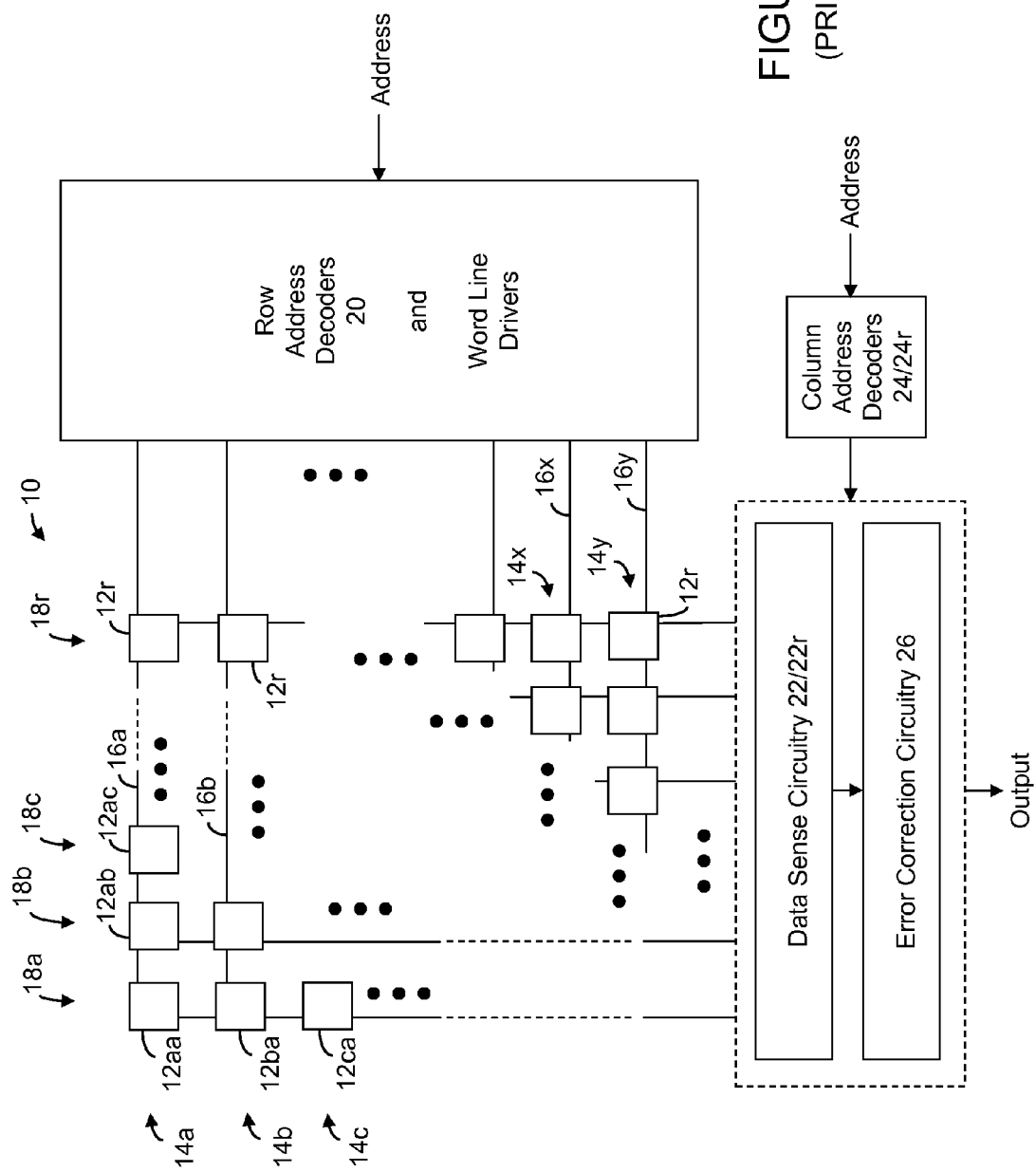
FIG. 1A is a schematic block diagram illustration of a conventional memory cell array having a plurality of memory cells arranged in an array of a plurality of rows and columns, in conjunction with row and column address decoders, word line drivers and data sense circuitry.
Figure 1B:
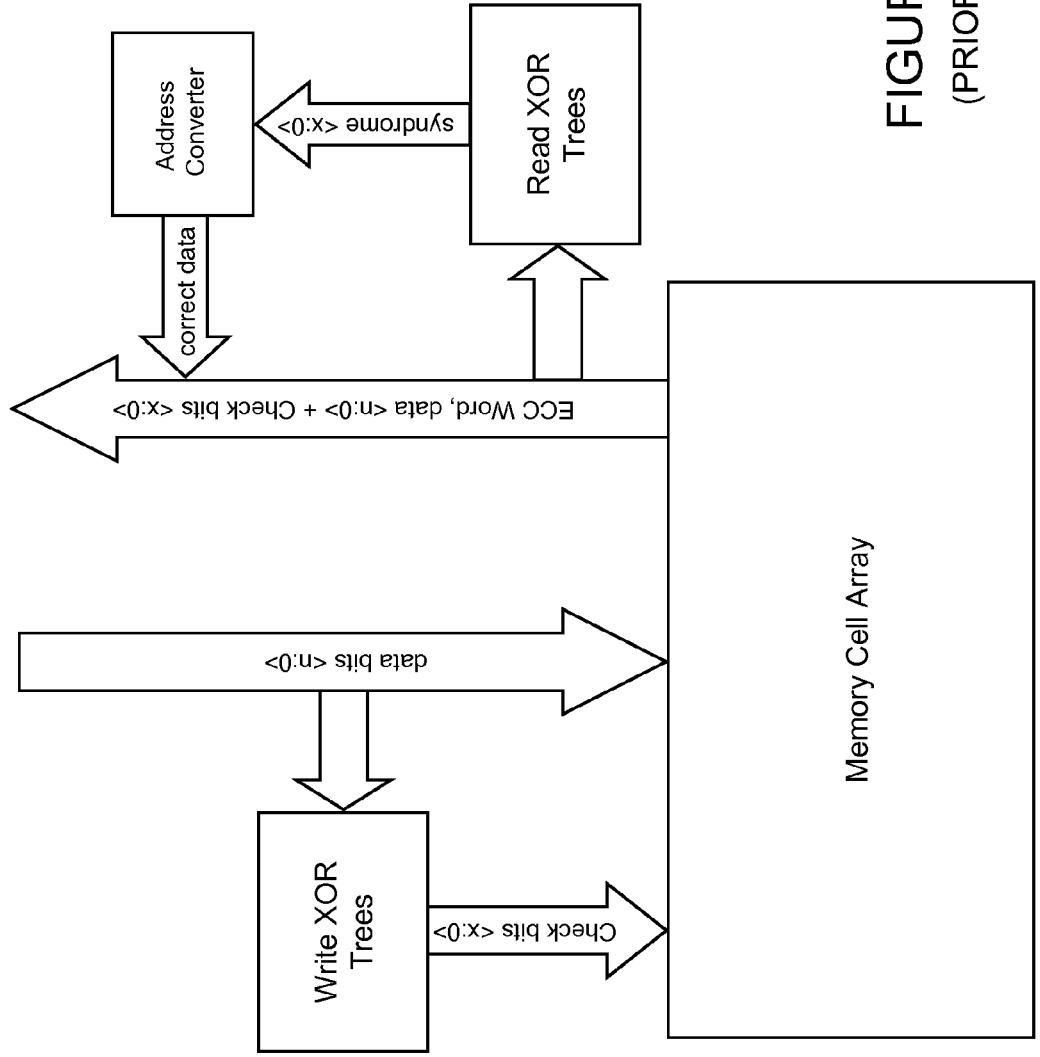
FIG. 1B is a schematic block diagram illustration of a conventional memory cell array in conjunction with a conventional ECC architecture including (i) a Read XOR tree in the read/output data path and (ii) a Write XOR tree in the input/write data path.

There are many inventions described and illustrated herein. In one aspect, the present inventions are directed to column redundancy and/or ECC architectures and techniques for a memory cell array having a plurality of memory cells, arranged in a matrix of rows and columns. In another aspect, the present inventions are directed to methods of programming, configuring, controlling and/or operating such column redundancy and/or ECC circuitry. The memory cell array, column redundancy circuitry, and/or ECC circuitry may comprise a portion of an integrated circuit device, for example, a logic device (such as, a microcontroller, microprocessor or the like) or a portion of a memory device (such as, a discrete memory device).

In certain embodiments of the inventions, the ECC architecture may make more efficient use of the ECC circuitry in that the read data path and the write data path may employ the same ECC circuitry. In this way, the present inventions may, among other things, provide a significant area and power reduction (relative to conventional architectures/techniques).

In addition, the column redundancy architectures implemented according to one or more aspects of the present inventions may make more efficient use of the pre-existing addressing circuitry (for example, the column pre-decoders and decoders). In this way, the present inventions may provide an even greater reduction of area and power (when used in combination) because, among other things, the redundant column address decoder may be eliminated. Such circuitry is often quite large, and often consuming as much area as the normal column decoders.

In yet another aspect, the present inventions are directed to combinations and permutations of the (i) ECC architectures and techniques and (ii) column redundancy architectures and techniques. Indeed, all such combinations and permutations are intended to fall within the scope of the present inventions.

Notably, the present inventions may be implemented in conjunction with any memory cell technology, whether now known or later developed. For example, the memory cells may include one or more transistors having electrically floating body regions, one transistor-one capacitor architectures, electrically floating gate transistors, junction field effect transistors (often referred to as JFETs), or any other memory/transistor technology whether now known or later developed. All such memory technologies are intended to fall within the scope of the present inventions.

Moreover, the present inventions may be implemented in conjunction with any type of memory (including discrete or integrated with logic devices), whether now known or later developed. For example, the memory may be a DRAM, SRAM and/or Flash. All such memories are intended to fall within the scope of the present inventions.

In one embodiment, the memory cells of the memory cell array may include at least one transistor having an electrically floating body transistor which stores an electrical charge in the electrically floating body region thereof. The amount of charge stored in the in the electrically floating body region correlates to the data state of the memory cell. One type of such memory cell is based on, among other things, a floating body effect of semiconductor on insulator (SOI) transistors. (See, for example, (1) Fazan et al., U.S. Pat. No. 6,969,662, (2) Okhonin et al., U.S. Patent Application Publication No. 2006/0131650 ("Bipolar Reading Technique for a Memory Cell Having an Electrically Floating Body Transistor"), (3) Okhonin et al., U.S. Patent Application Publication No. 2007/0058427 ("Memory Cell and Memory Cell Array Having an Electrically Floating Body Transistor, and Methods of Operating Same"), (4) Okhonin, U.S. patent application Ser. No. 11/633,311, filed Dec. 4, 2006, and entitled "Electrically Floating Body Memory Cell and Array, and Method of Operating or Controlling Same", and (5) Okhonin et al., U.S. patent application Ser. No. 11/703,429, filed on Feb. 7, 2007, and entitled "Multi-Bit Memory Cell Having Electrically Floating Body Transistor, and Method of Programming and Reading Same", all of which are incorporated by reference herein in their entirety). In this regard, the memory cell may consist of a partially depleted (PD) or a fully depleted (FD) SOI transistor or bulk transistor (transistor which formed in or on a bulk material/substrate) having a gate, which is disposed adjacent to the electrically floating body and separated therefrom by a gate dielectric. The body region of the transistor is electrically floating in view of the insulation or non-conductive region, for example, in bulk-type material/substrate, disposed beneath the body region. The state of memory cell may be determined by the concentration or amount of charge contained or stored in the body region of the SOI or bulk transistor.

With reference to FIG. 2, the ECC architecture according to one embodiment of the present inventions includes multiplexer circuitry 50 and syndrome generation circuitry 52. The multiplexer circuitry 50 includes a plurality of multiplexers 50a-n which receive, at one input, $D_{in}$<n> (for example, input data received during, for example, a write operation), and at another input, $D_{out}$<n> (for example, output data obtained during, for example, a read operation). In addition, depending on the type of operation, multiplexers 50w-x may receive certain check bit related data. The plurality of multiplexers 50a-n and 50w-x may be responsive to a control signal "Data Select".

Figure 3:
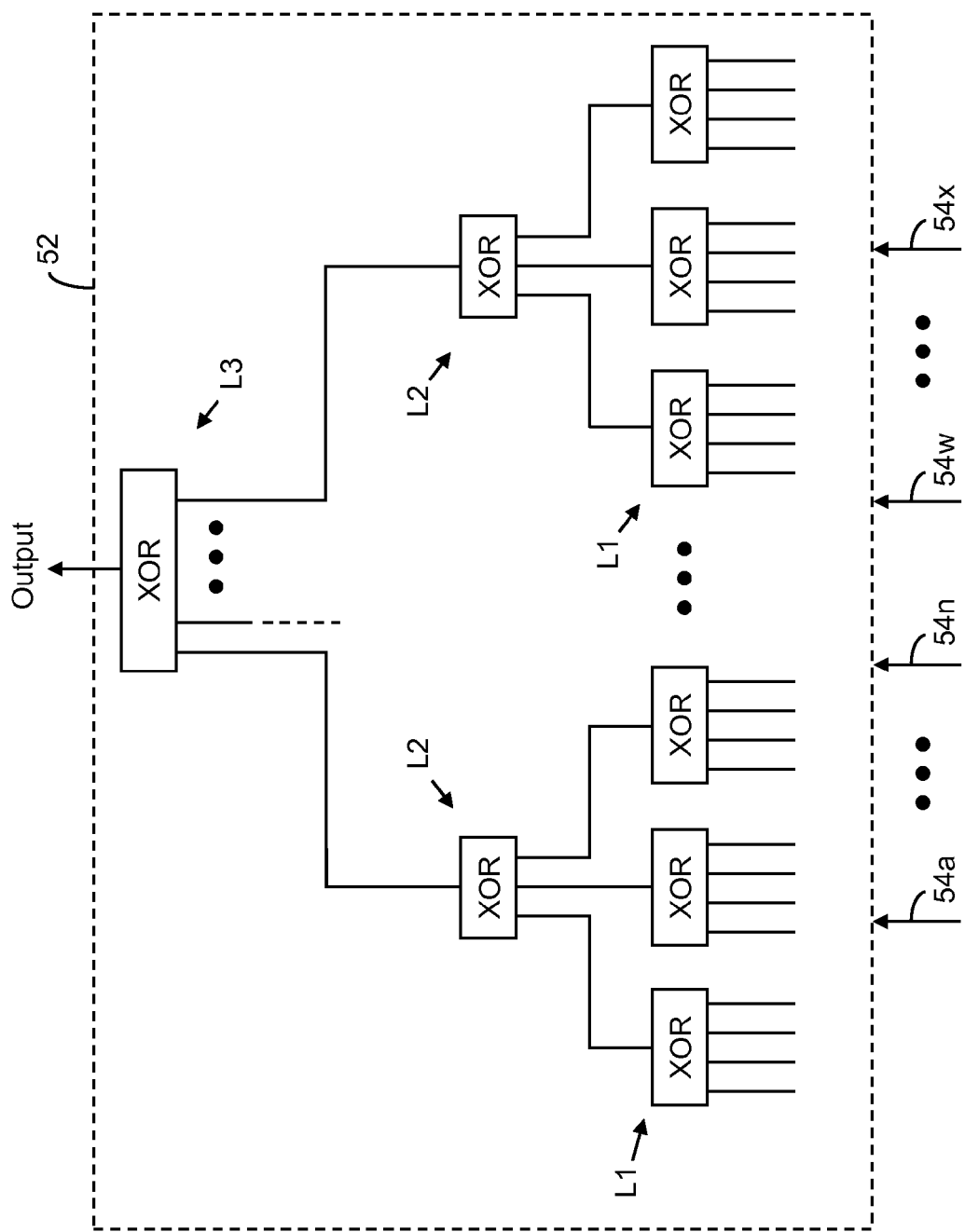
FIG. 3 is a schematic block diagram illustration of exemplary syndrome generation circuitry, according to an aspect of the present inventions.

The outputs 54a-n and 54w-x of multiplexers 50a-n and 50w-x, respectively, are provided to syndrome generation circuitry 52 which generates a syndrome vector. In one embodiment, with reference to FIG. 3, syndrome generation circuitry 52 includes a plurality of XOR logic gates. In this embodiment, the plurality of XOR logic gates are arranged in XOR logic levels, including a first level L1, second level L2 and third level L3. Notably, any circuitry, architecture and technique for generating syndrome vector data, whether now known or later developed, is intended to fall within the scope of the present inventions.

With continued reference to FIG. 2, with respect to the check bit related data, during a read operation, multiplexers 50w-x receive check bit data from the memory cell array and provide the check bit data (via outputs 54w-x), for the given output data, to syndrome generation circuitry 52. In contrast, during a write operation, the inputs associated with the "check bits" may be set to a predetermined value (for example, logic "zero") to facilitate generation of new check bits. (See, multiplexers 50w-x of FIG. 2). As such, in this aspect of the inventions, syndrome generation circuitry 52 is shared during read and write operations.

Figure 4A:
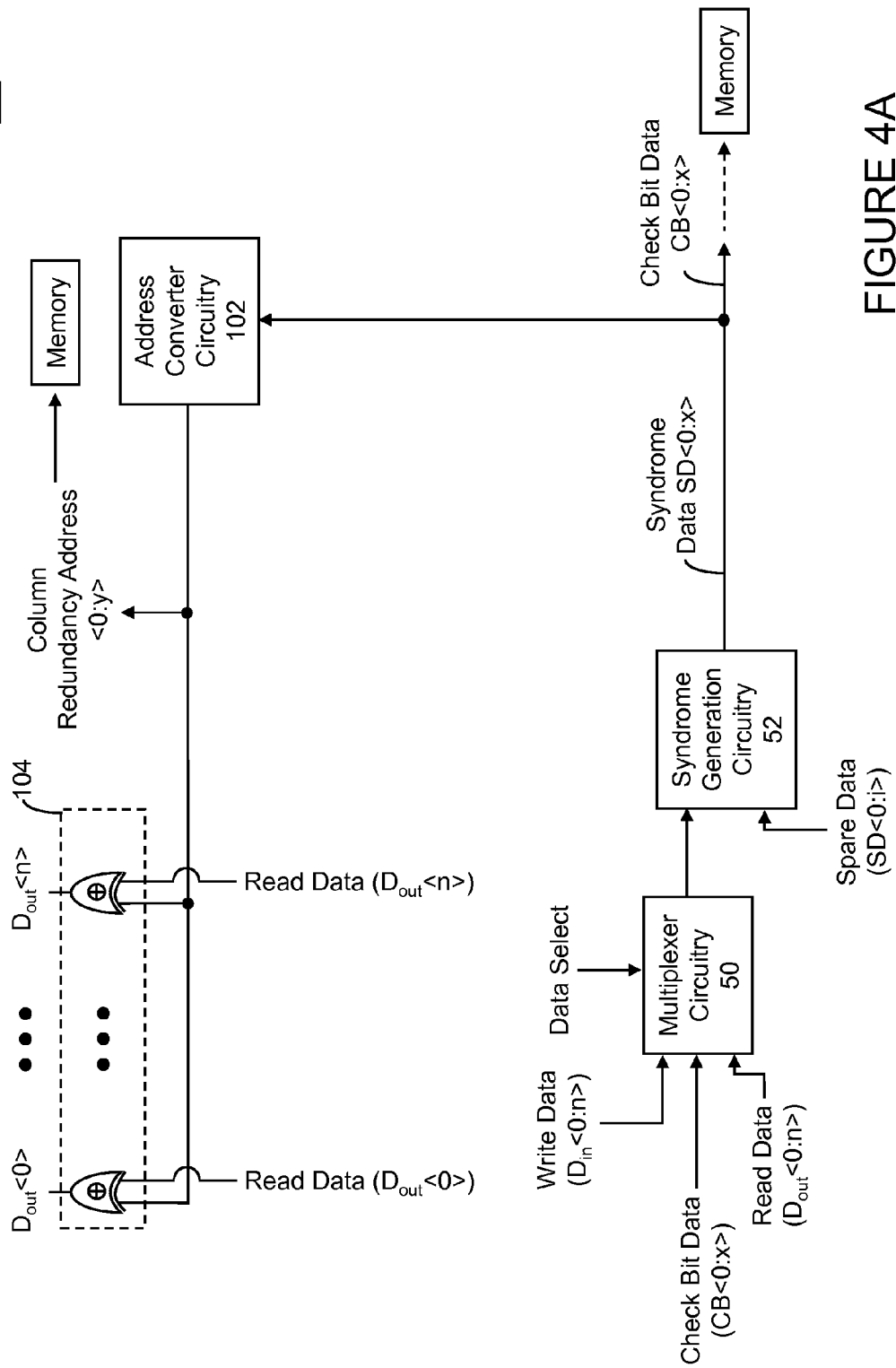
FIGS. 4A and 4B are schematic block diagram illustrations of, among other things, circuitry to program a column redundancy architecture using ECC architectures.
Figure 4B:
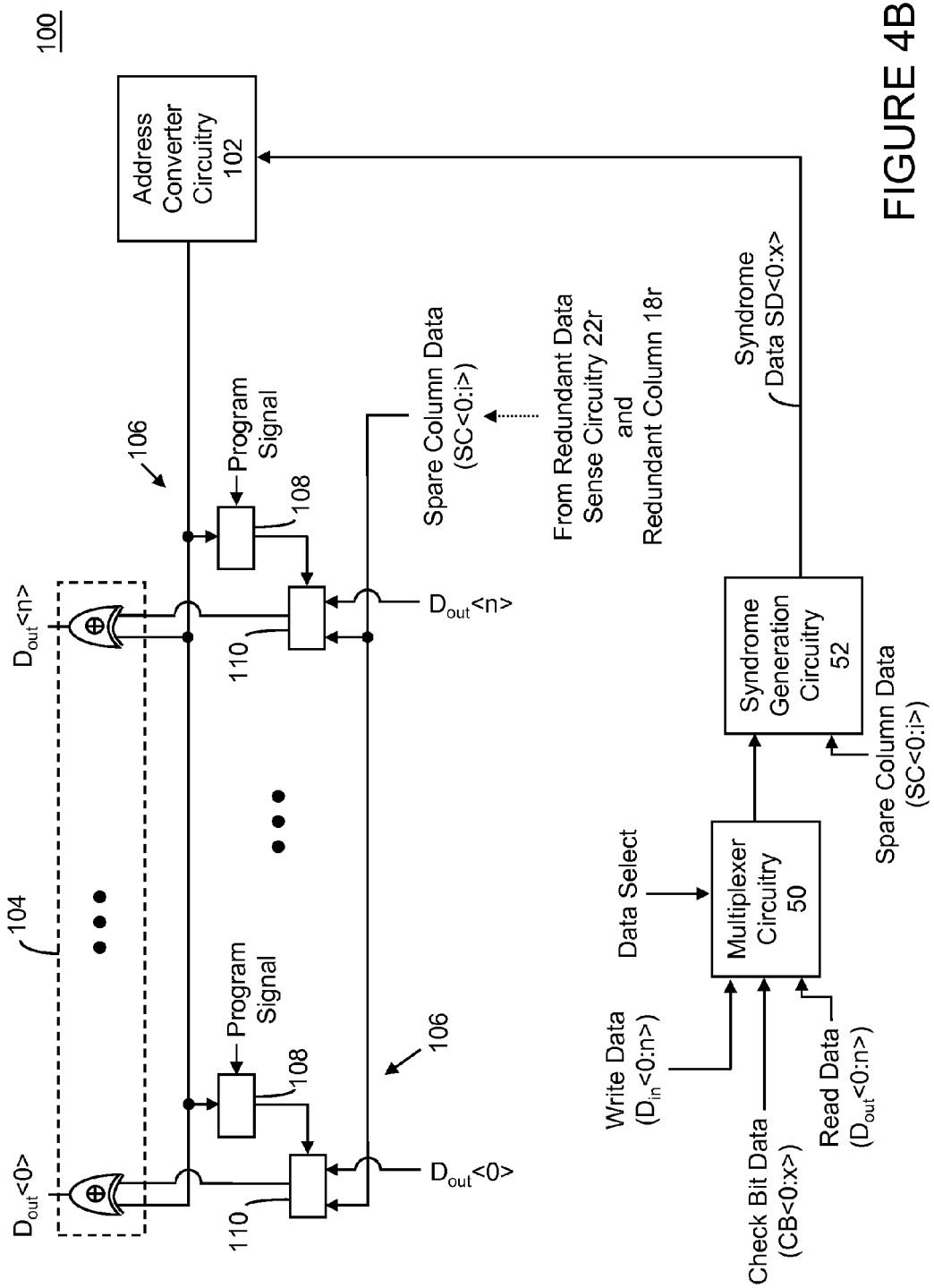
Figure 5:
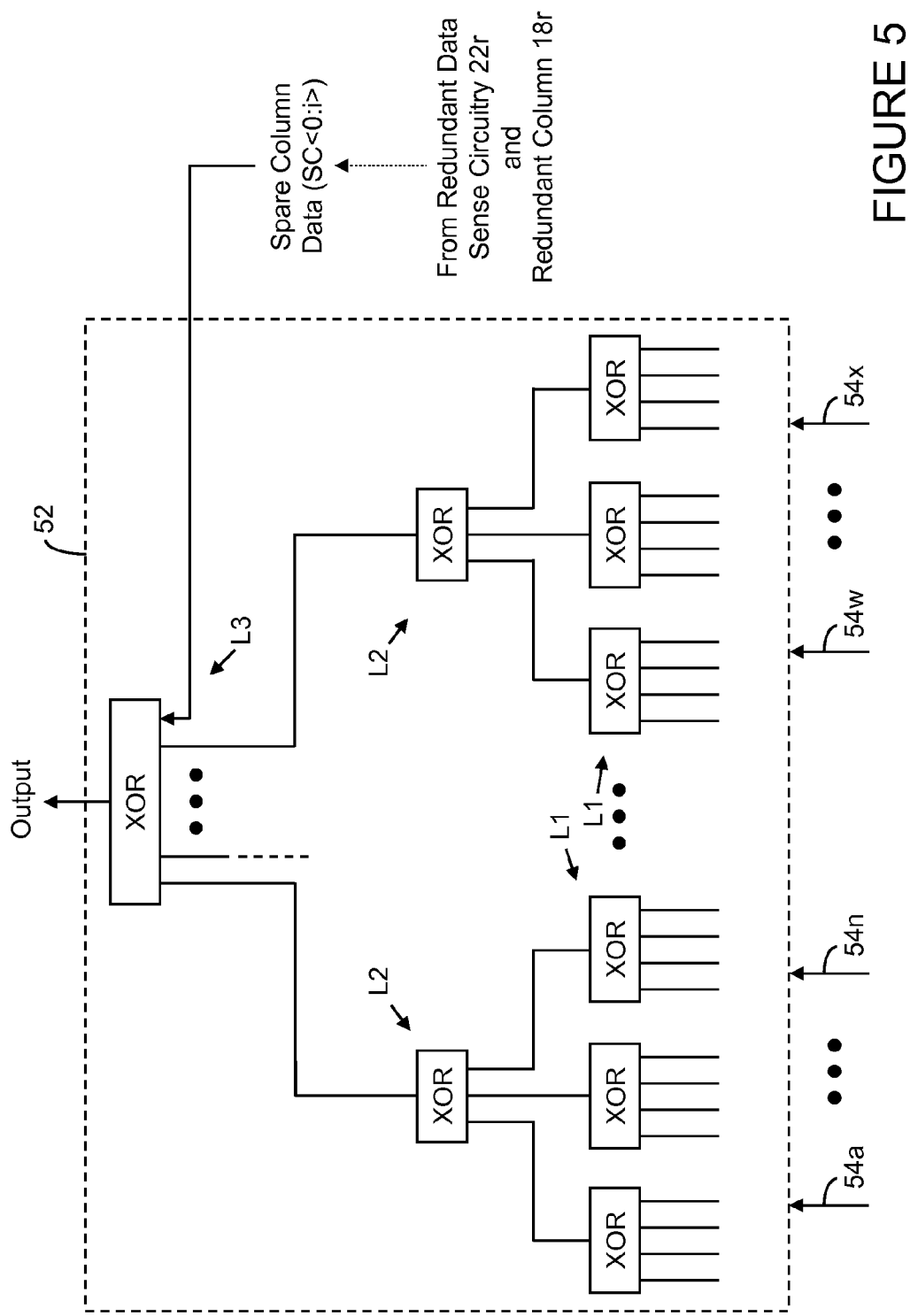
FIG. 5 is a schematic block diagram illustration of exemplary syndrome generation circuitry of FIGS. 4A and/or 4B, according to an aspect of the present inventions, wherein column redundancy data is provided to the last stage of the syndrome generation circuitry, according to an aspect of the present inventions.

In aspect of the inventions, the ECC architecture is implemented in conjunction with column redundancy circuitry. With reference to FIGS. 4A, 4B and 5, in one embodiment, system 100 includes the ECC architecture of FIGS. 2 and/or 3 in conjunction with column redundancy circuitry. In this embodiment, the output data from spare column(s) 18r is/are provided to syndrome generation circuitry 52. In one embodiment, with reference to FIG. 5, the output of the spare column 18r (here illustrated as one spare column and one output) is provided to the last level or stage of the XOR logic of syndrome generation circuitry 52. In this way, the latency of the ECC operation may be eliminated, reduced and/or minimized because the output data from spare column 18r is often "slower" than the bits from the "normal" columns 18. As such, syndrome generation circuitry 52 may generate a syndrome vector more rapidly, which may be critical to the "speed path" of system 100.

Notably, when spare column 18r is not in use, the output of spare column 18r is set to a logic state which minimizes or eliminates any impact on the ECC architecture/operation by the output data of spare column 18r (here, logic "zero"). Similarly, when spare column 18r is in use (for example, spare column 18r is substituting for or replacing a defective column (for example, 18d "d" for "defective") in array 10), the output of column 18d is set to a logic state which eliminates or minimizes the impact on the ECC architecture/operation by the defective column (here again, logic "zero"). In this way, syndrome generation circuitry 52 generates correct syndrome data (SD<0:x>).

With reference to FIG. 4A, in one embodiment, the column redundancy architecture may be programmed using, among other things, address converter circuitry 102. In this regard, in one exemplary embodiment, the syndrome data generated, provided and/or output by syndrome generation circuitry 52 is provided to address converter circuitry 102 which decodes the syndrome data (SD<0:x>) to indicate the position of the erroneous bit in the ECC data (ECC<0:z>). In this embodiment, the syndrome data includes information which is representative of the address of the erroneous bit in a single error detection and correction ECC technique using Hamming Code. Notably, the address map of the ECC data often does not correspond to the physical location of the bits in memory cell array 10 because, for example, the check bit data (CB<0:x>) may be stored with the actual data bits in memory, for example, memory cell array 10. This tends to alter the logical bit location (indicated by the syndrome data) from the physical bit location (indicated by the redundancy address or the address of the faulty column). As such, address converter circuitry 102 may include a circuit (for example, a look-up table) and/or technique (for example, a logic-physical translation programming technique) to correlate the logical bit location (indicated by the syndrome data) from the physical bit location (indicated by the redundancy address).

With continued reference to FIG. 4A, address converter circuitry 102 generates address data (column redundancy address <0:y>) which corresponds to the defective column—i.e., the column having, for example, one or more defective or inoperative memory cells and/or data sense circuitry 22. The redundant column address data may be employed by other circuitry to replace or substitute column 18 having, for example, one or more defective or inoperative memory cells and/or data sense circuitry, by a spare column 18r.

The column redundancy address data may be stored in a memory which may be any circuitry, whether now known or later developed, that stores data (here, the redundant column address). For example, the memory may be one or more fuses or anti-fuses, or DRAM, SRAM, PROM, EPROM, EEPROM cells, and/or latch or register circuitry (for example, a plurality of latches or registers). Notably, all forms or types of memory, whether now known or later developed, are intended to fall within the scope of the present inventions.

The address converter circuitry 102 may be, for example, a microprocessor, microcontroller, state machine, discrete logic, and/or programmable gate array (for example, field programmable gate array). The address converter circuitry 102 may include any circuitry and/or implement any technique, whether now known or later developed, which decodes the syndrome data to indicate the position of the erroneous bit.

In one embodiment, system 100 further includes a plurality of redundancy program circuits connected to logic gates which output the corrected output data. For example, with reference to FIG. 4B, in one embodiment, at least one redundancy program circuit 106 is connected in an associated data path and to an associated logic gate 106 which outputs the corrected output data. The redundancy program circuit 106 responsively couples either the output data of the normal column 18 or the output data of the spare column 18r (via redundant sense circuitry 22r) to the output drivers (not illustrated).

In one embodiment, redundancy program circuitry 106 includes memory circuit 108 and a selection circuit 110 (for example, a multiplexer). The memory circuit 108 (in response to a program signal) stores or maintains data/information which represents or indicates that a particular column 18 has been replaced or substituted by a spare column 18r. In one embodiment, memory circuit 108 is a latch which is programmed when address converter circuitry 102 identifies a particular column 18 to be replaced or substituted by a spare column 18r. In this regard, as mentioned above, in one exemplary embodiment, the syndrome data includes information which is representative of the address of the erroneous bit in a single error detection and correction ECC technique using Hamming Code. The address converter circuitry 102 decodes the syndrome data (SD<0:x>) to indicate the position of the column 18 to be replaced or substituted, via the column redundancy, with a spare column 18r. In response to detecting the position of the erroneous bit, address converter circuitry 102 provides, programs and/or stores (via the program signal) data/information in memory circuit 108 to represent or indicate that a particular column 18 has been replaced or substituted by a spare column 18r.

In normal operation, with reference to FIG. 4B, in response to detecting the position of the erroneous bit, address converter circuit 102 provides data/information to one or more logic gates 104 such that any erroneous bit(s) is/are corrected prior to being output by system 100. In one embodiment, logic gates 104 include a plurality of XOR gates. Under these circumstances, address converter circuit 102 provides a logic "high" signal to the XOR gate corresponding to or associated with the erroneous bit position (for example, bit position "y"), such that the output data ($D_{out}$<y>) gets inverted (and hence corrected) and logic gates 104 output ECC data (ECC<0:z>).

The data/information stored in the memory circuit 108 controls selection circuitry 110. In this regard, where the data/information in memory circuit 108 indicates that a column 18 is replaced or substituted by a spare column 18r, selection circuitry 110 provides or outputs the spare column data (SC<i>) to an associated logic gate of logic gates 104. As such, in operation, the predetermined spare column is coupled to the output path such that the spare column data (SC<i>) is output to the appropriate data path when the data/information in memory circuit 108 indicates that spare column 18r corresponds to, or replaces or substitutes for the normal column 18.

Notably, although memory circuits 108 are illustrated as distributed among redundancy program circuit 106, such memory circuitry may be integrated in one or more areas. In this regard, system 100 may employ any circuitry and/or architecture, whether now known or later developed, to store or maintain the data/information which represents or indicates that a particular column 18 has been replaced or substituted by a spare column 18r. For example, the circuit may be one or more fuses or anti-fuses, or DRAM, SRAM, PROM, EPROM, EEPROM cells, and/or latch or register circuitry (for example, a plurality of latches or registers). Notably, all forms or types of memory and architectures, whether now known or later developed, are intended to fall within the scope of the present inventions.

Further, memory circuits 108 may be one time programmable (for example, programmed during test or at manufacture) or more than one time programmable (for example, during test, start-up/power-up, during an initialization sequence and/or during operation (in situ)). For example, in one embodiment, memory circuits 108 may be programmed, for example, (i) during test, at start-up/power-up and/or during an initialization sequence (and thereafter fixed) or (ii) in situ, at start-up/power-up and/or during an initialization sequence (and thereafter re-programmable).

As noted above, the column redundancy architecture may be programmed using address converter circuitry 102 and the syndrome data generated, provided and/or output by syndrome generation circuitry 52. Here, the address converter circuitry 102 decodes the syndrome data (SD<0:x>) to indicate the position of the erroneous bit in the ECC data (ECC<0:z>). In this embodiment, the syndrome data includes information which is representative of the address of the erroneous bit in a single error detection and correction ECC technique using Hamming Code. Because the logical bit location (indicated by the syndrome data) differs from the physical bit location (indicated by the redundancy address), address converter circuitry 102 may include a circuit (for example, a look-up table) and/or technique (for example, a logic-physical translation programming technique) to correlate the logical bit location (indicated by the syndrome data) from the physical bit location (indicated by the redundancy address). Also mentioned above, address converter circuitry 102 may be, for example, a microprocessor, microcontroller, state machine, discrete logic, and/or programmable gate array (for example, field programmable gate array) and/or any circuitry, whether now known or later developed, to decode the syndrome data to indicate the position of the erroneous bit in the ECC data is intended to fall within the scope of the present inventions.

Figure 6A:
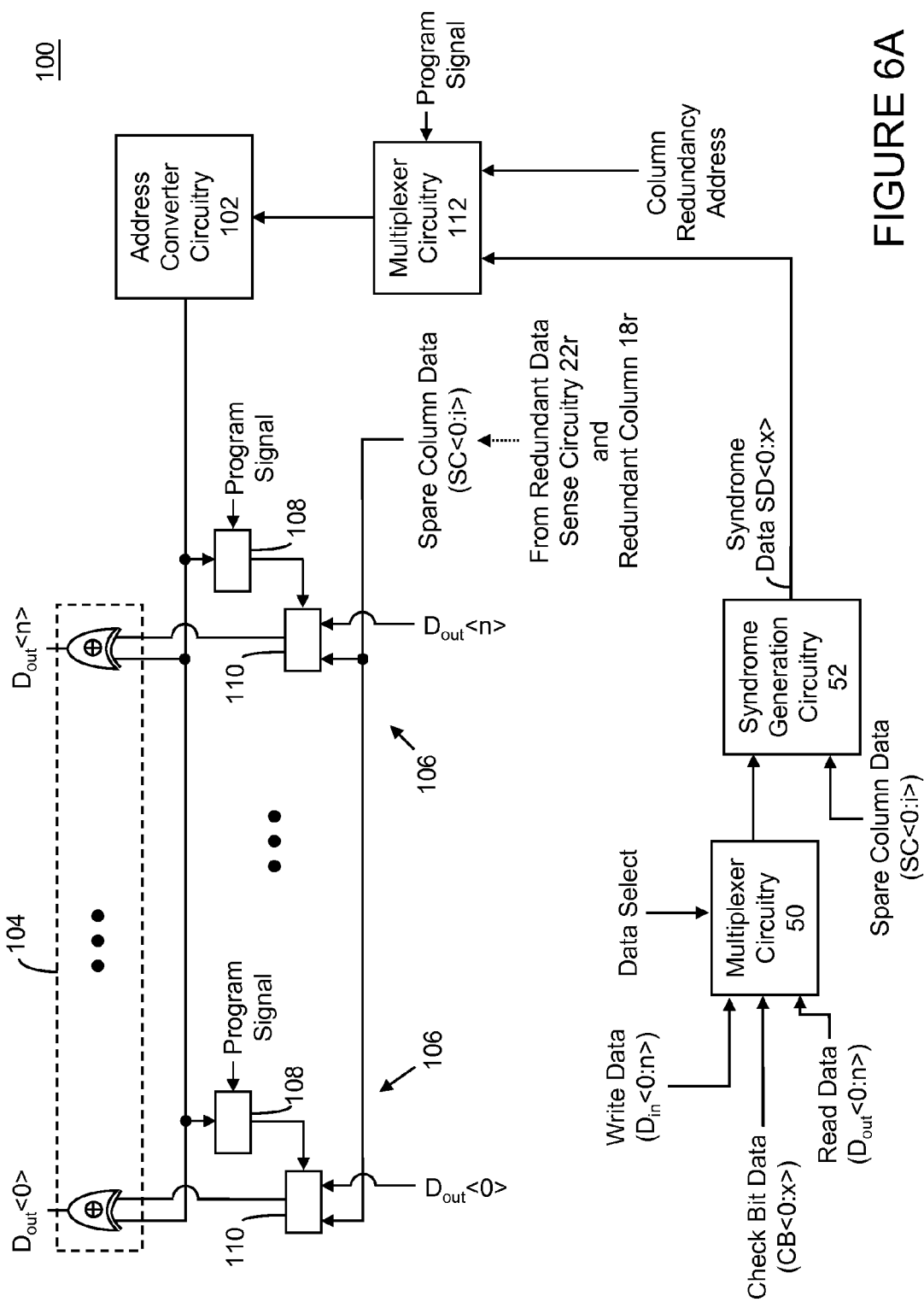
FIGS. 6A-6D are schematic block diagram illustrations of, among other things, circuitry to program a column redundancy architecture, using the ECC architecture, controller circuitry and/or external circuitry, in conjunction with column redundancy circuitry, according to an aspect of the present inventions.

The address(es) of the column(s) of memory cells to be "replaced" or "substituted" by the redundant or spare column(s) of memory cells may be provided and/or determined by internal/integrated circuitry (i.e., on-chip) (see, for example, FIGS. 4A and 4B) or external (i.e., off-chip—for example, on a different integrated circuit device which, for example, is disposed or resident on a common printed circuit board). For example, with reference to FIG. 6A, in another embodiment, one or more column redundancy addresses are provided to address converter circuitry 102 to program redundancy program circuits 106 accordingly. In this mode, address converter circuitry 102 may then program redundancy program circuit 106 accordingly. Notably, in those instances where the column redundancy address is a physical address, address converter circuitry 102, in a redundancy programming mode, may not translate the column redundancy address before programming the redundancy program circuits 106. Under these circumstances, address converter circuitry 102 includes circuitry to program redundancy program circuits 106 without converting a logical address to a physical address.

Notably, in a "normal" mode, address converter circuitry 102 handles the ECC cases/situations. In this regard, address converter circuitry 102 converts syndrome vector to the logical bit position.

In operation, during programming of the column redundancy circuitry, multiplexer circuitry 112 may provide the column redundancy address data to address converter 102 which employs that data to program the redundancy program circuits 106. The multiplexer circuitry may be responsive to the program signal or another programming control signal. Notably, during normal operation, multiplexer circuitry 112 provides the ECC data (ECC<0:z>) to logic gates 104.

As mentioned above, during normal operation, in response to detecting the position of the erroneous bit, address converter circuit 102 provides data/information to one or more logic gates 104 such that any erroneous bit(s) is/are corrected prior to being output by system 100. In one embodiment, logic gates 104 include a plurality of XOR gates. Under these circumstances, address converter circuit 102 provides a logic "high" signal to the XOR gate corresponding to or associated with the erroneous bit position (for example, bit position "y"), such that the output data ($D_{out}$<y>) gets inverted (and hence corrected).

Figure 6B:
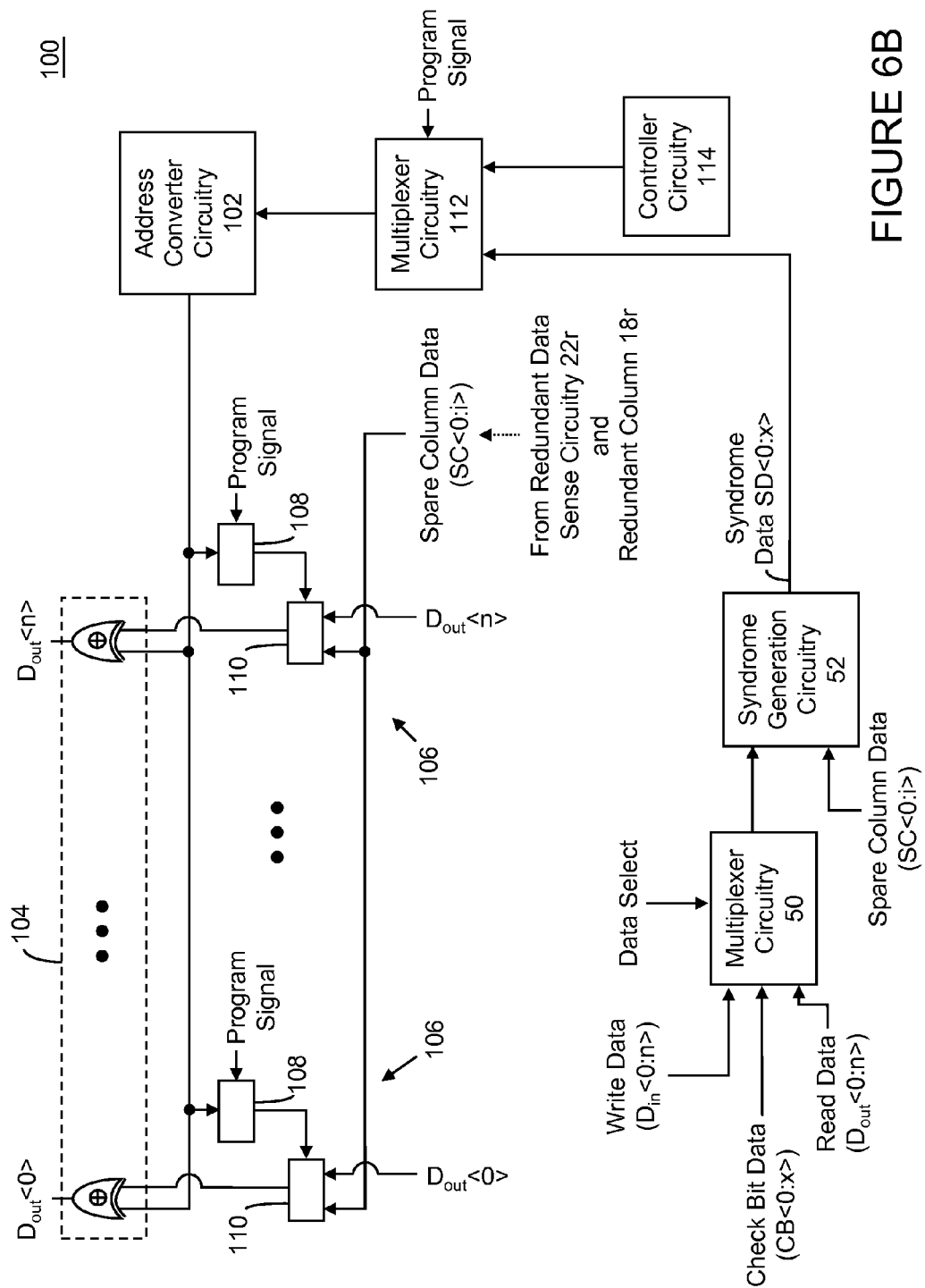

As noted above, the column redundancy address(es) may be provided and/or determined via internal/integrated circuitry (i.e., on-chip) or external (i.e., off-chip—for example, in a separate or different integrated circuit device which, for example, is disposed or resident on a common printed circuit board). Where the circuitry which detects one or more columns of memory cells to be "replaced" or "substituted" by one or more redundant or spare columns is internal/integrated on the same die as the memory cell array and the column redundancy circuitry, the column address data (which correspond to one or more column addresses of memory cells including, for example, one or more defective or inoperative memory cells) may be provided by a controller at, for example, start-up/power-up, during an initialization sequence and/or during operation. With reference to FIG. 6B, in one embodiment, controller circuitry 114 (for example, built-in self-test (BIST) circuitry) may be employed to detect one or more defective or inoperative memory cells and/or data sense circuitry 22 of memory cell array 10. In response to detecting one or more memory cells to be "replaced", controller circuitry 114 may place system 100 in a programming mode and apply the associated column address or addresses of such memory cells to address converter circuitry 102 which, as mentioned above, programs (or re-programs), maintains and/or stores (via the program signal) data/information in memory circuit 108.

Notably, the programming of the redundancy program circuit (for example, by controller circuitry 114) may be a one-time process, for example, during start-up/power-up and/or during an initialization sequence. The programming may also be in situ, for example, in response to detection of a bit failure or anticipated bit failure by controller circuitry 114, for example, during operation of the memory cell array 10.

The controller circuitry 114 may be any type of circuitry (whether hardwired or programmable) that may detect one or more defective or inoperative memory cells. For example, controller circuitry 114 may be external (non-integrated) circuitry or internal (integrated) circuitry, such as, for example, BIST circuitry. (See, for example, "A 30-ns 64-MB DRAM with Built-in Self-Test and Self-Repair Function", Tanabe et al., IEEE Journal of Sold-Sate Circuits, Vol. 27, No. 11, November 1992, pp. 1525-1533). Notably, all forms or types of circuitry that are suitable to detect one or more defective or inoperative memory cells, whether now known or later developed, are intended to fall within the scope of the present inventions.

Figure 6C:
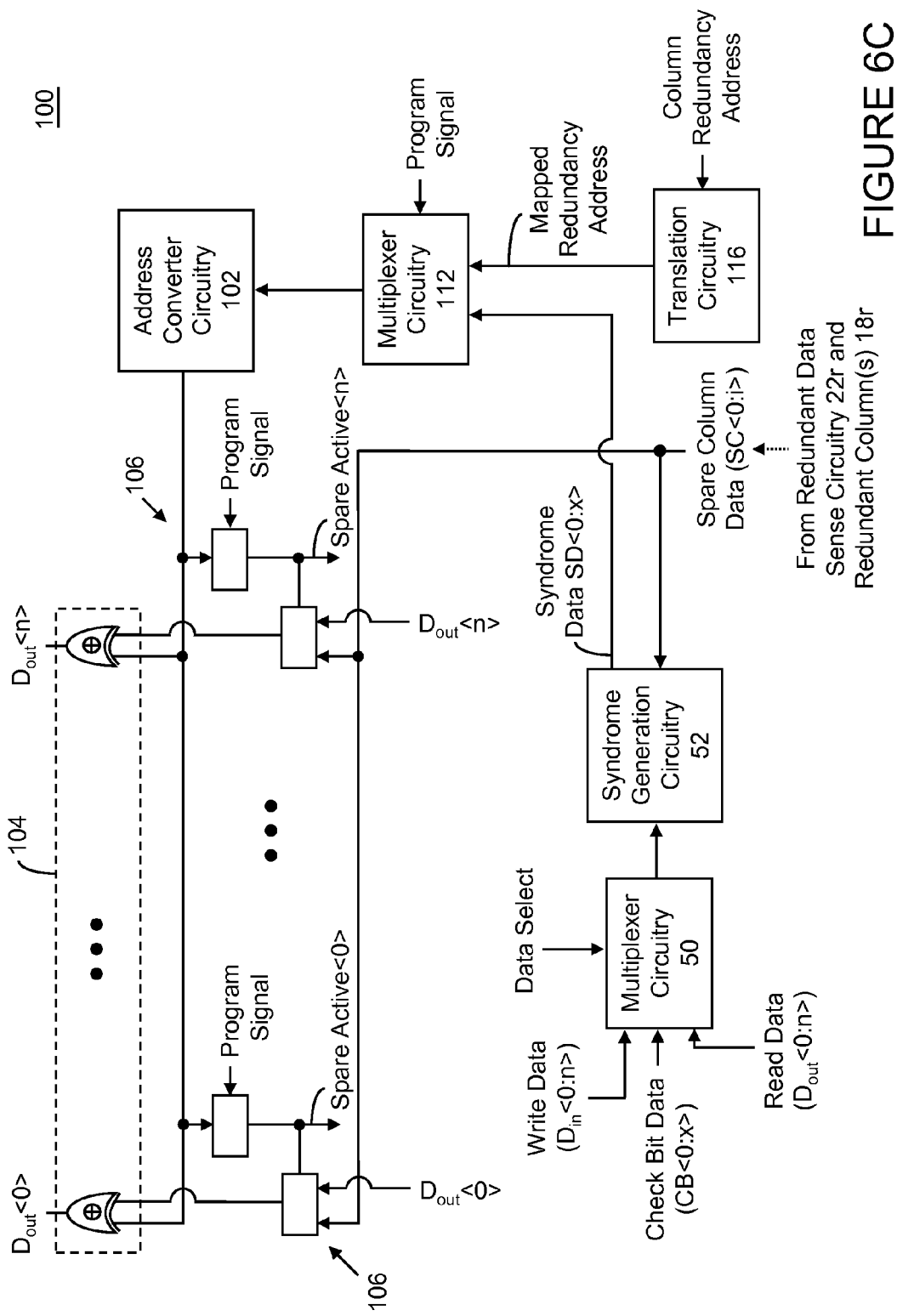

In certain embodiments, it may be advantageous to employ translation circuitry (for example, a ROM having a suitable look-up table) to "map" or translate an address which may be a non-physical address to a physical address. With reference to FIG. 6C, in one embodiment, a column address is applied to translation circuitry 116 which outputs a physical address to multiplexer circuitry 112. As such, in this embodiment, the translation of a logical address to a physical address is performed by translation circuitry 116 rather than address converter circuitry 102.

Notably, all of the embodiments described and illustrated herein may be employed in conjunction with translation circuitry 116 of FIG. 6C (for example, the embodiment of FIG. 6B). For the sake of brevity, those combinations and permutations will not be discussed in detail.

Figure 6D:
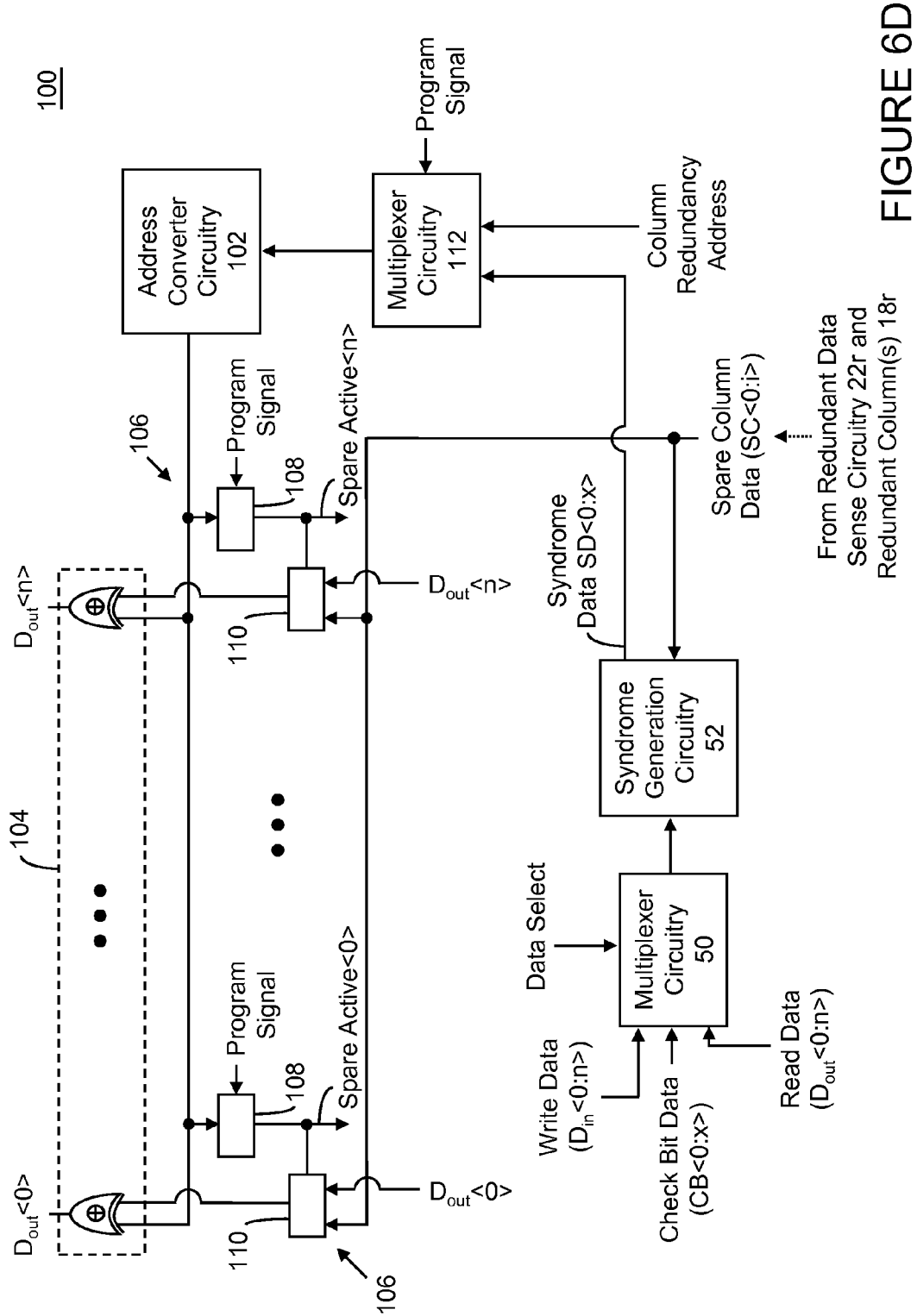
Figure 7:
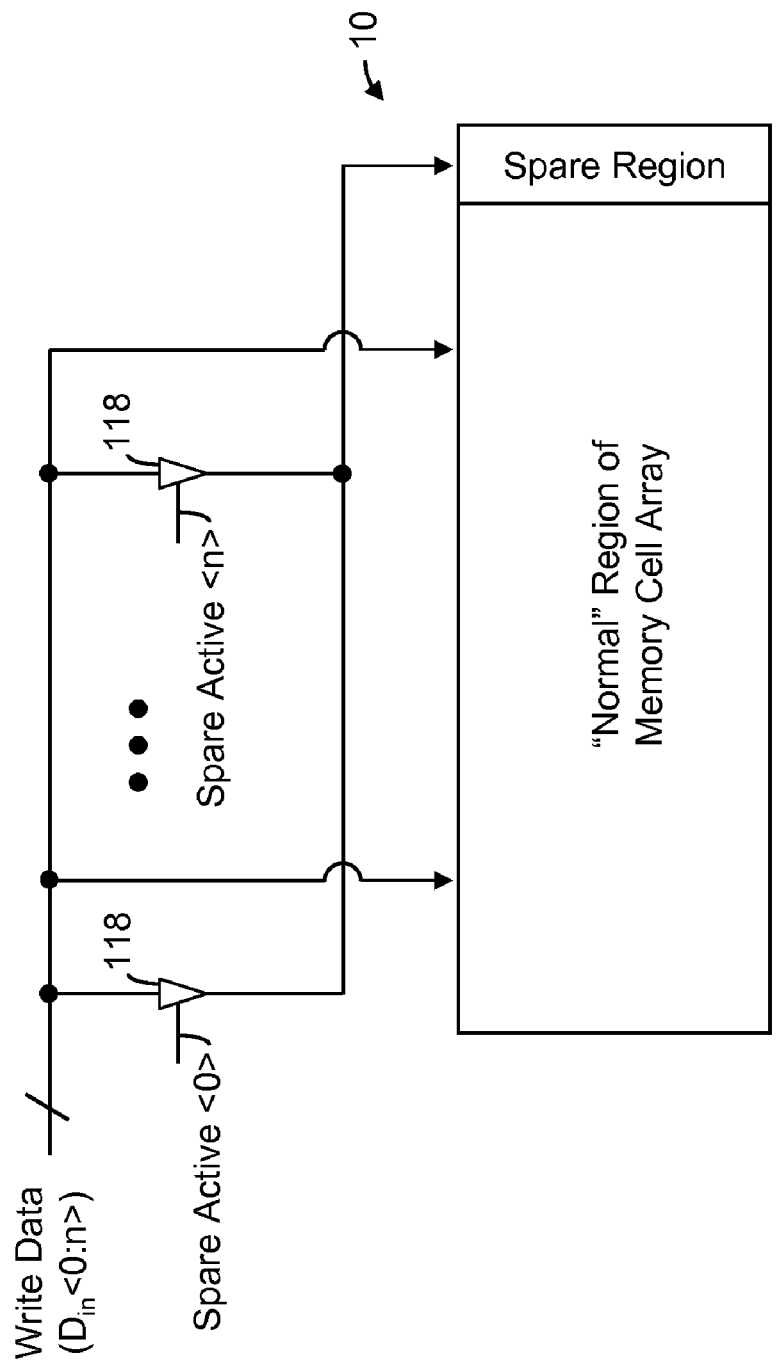
FIG. 7 is a schematic block diagram illustration of an exemplary implementation of a column redundancy architecture to control the writing of data into the normal section of the memory array and the spare section of the memory array, according to an aspect of the present inventions.

In another embodiment, data/information stored, maintained and/or programmed in memory circuit 108 is also provided to circuitry in the data input path to control the writing of data into memory cell array 10. For example, with reference to FIGS. 6D and 7, in one embodiment, the data/information which represents or indicates that a particular column 18 has been replaced or substituted by a spare column 18r (which is maintained in memory circuit 108) is employed to control a plurality of input drivers 118 which are associated with a spare column (here, generally illustrated as spare region of memory cell array 10). The input driver circuits 118 may be tri-state drivers which are enabled by a Spare Active control signal. In operation, the data input path of a spare column 18r may be activated when memory circuit 108 is programmed (using any of the techniques or embodiments discussed herein). As such, during a write operation, the data directed to the defective column 18 is written into the spare column 18r. Moreover, during a read operation, data may be read from the predetermined memory cell 10r in the spare column 18r. In this way, the defective column 18 is swapped with spare column 18r.

Figure 8A:
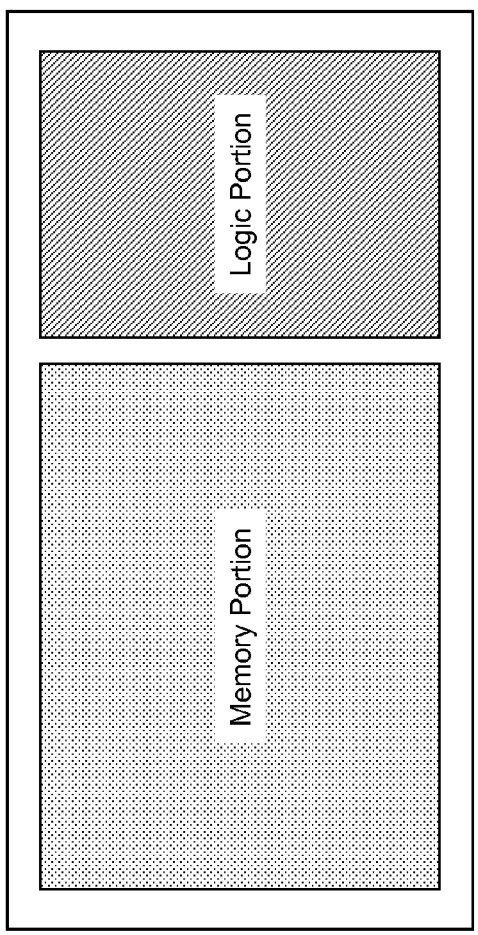
Figure 8B:
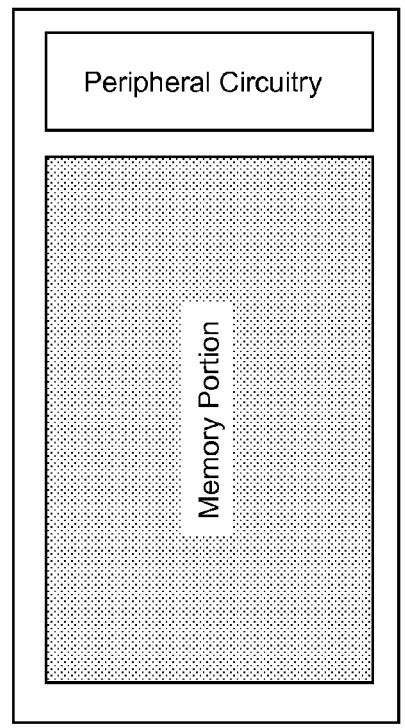
Figure 8C:
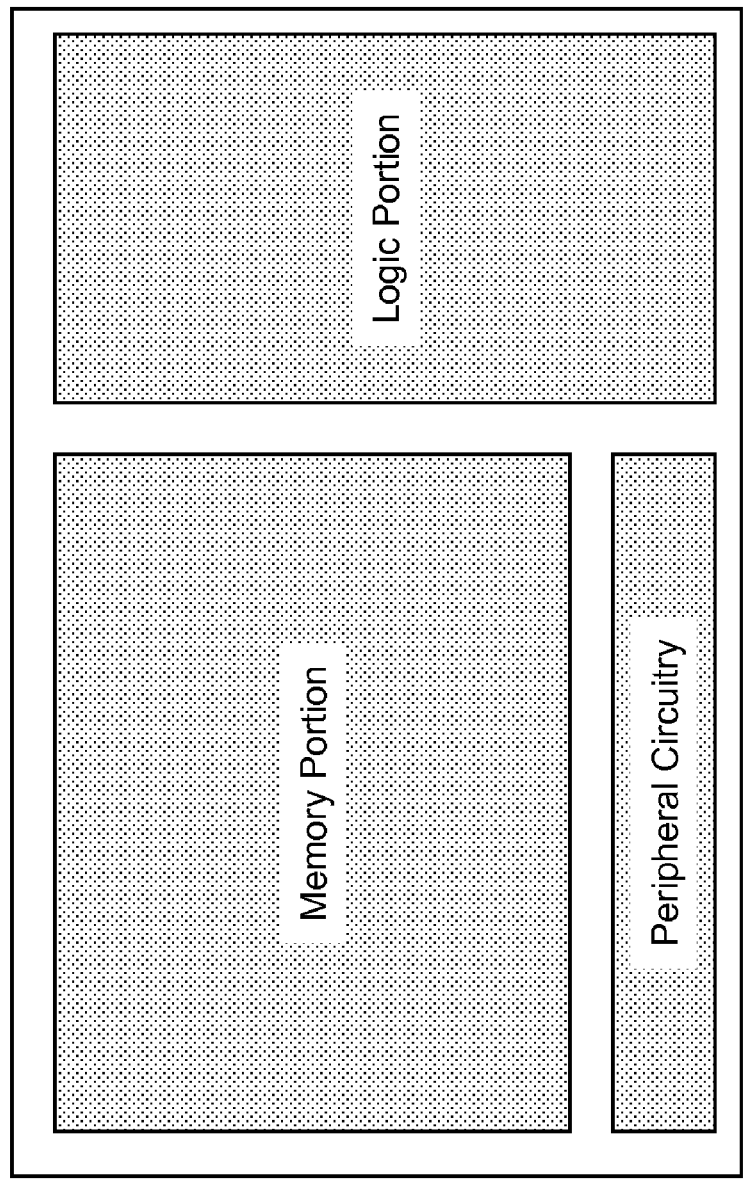
Figure 9:
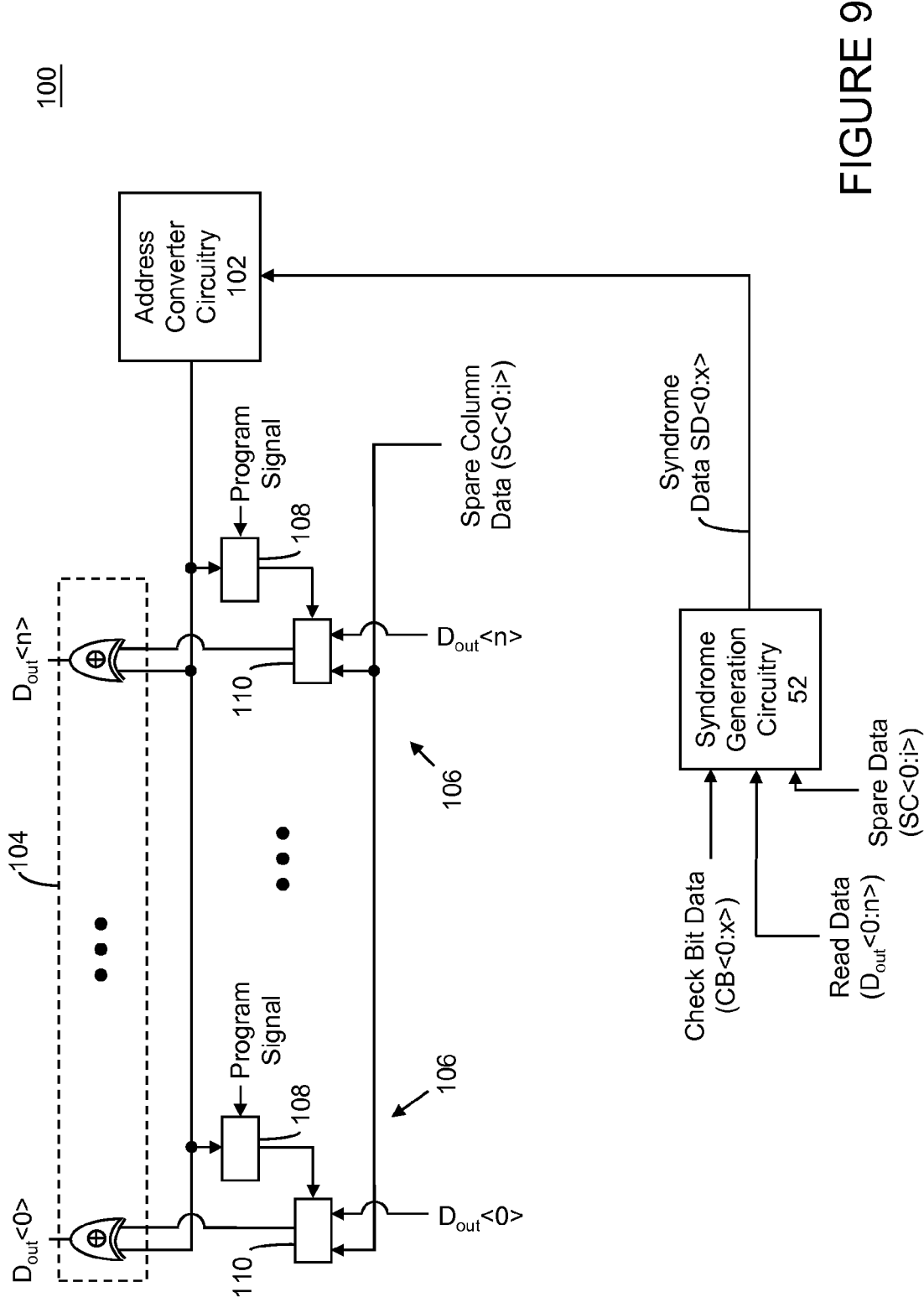
FIGS. 9, 10A-10C, and 11A-11C are exemplary schematic block diagram illustrations of, among other things, circuitry to program a column redundancy architecture using ECC architectures wherein the syndrome generation circuitry is not shared between the input and output paths (FIGS. 9, 10B and 10C), wherein the syndrome generation circuitry is shared between the input and output paths and a physical defective column address is provided to the redundancy program circuits (FIG. 10A), and wherein address converter circuitry employs syndrome data to program column redundancy architecture which also programs the input data path of the redundant columns in the memory cell array (FIGS. 9, 10C and 11A-11C).
Figure 10A:
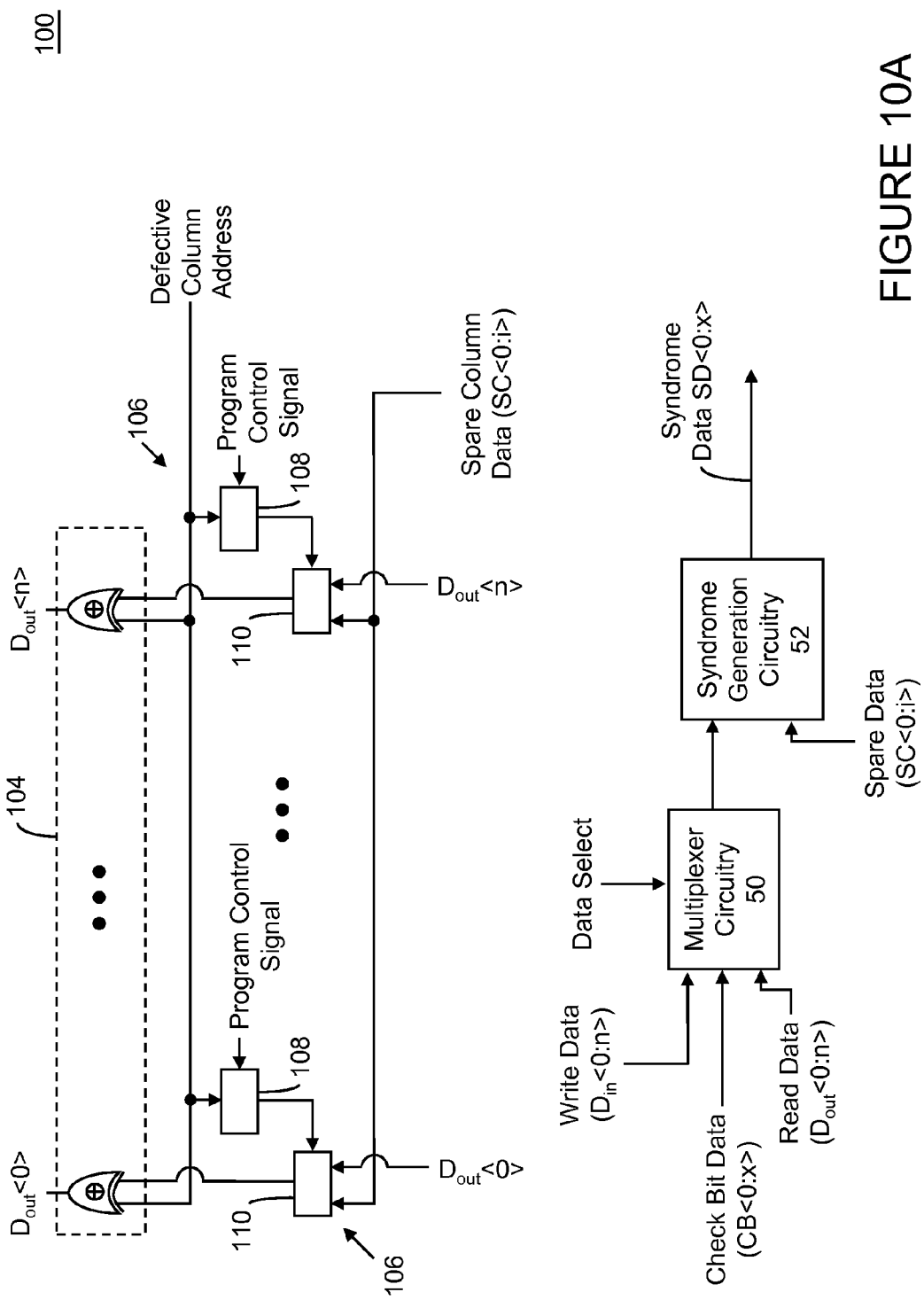
Figure 10B:
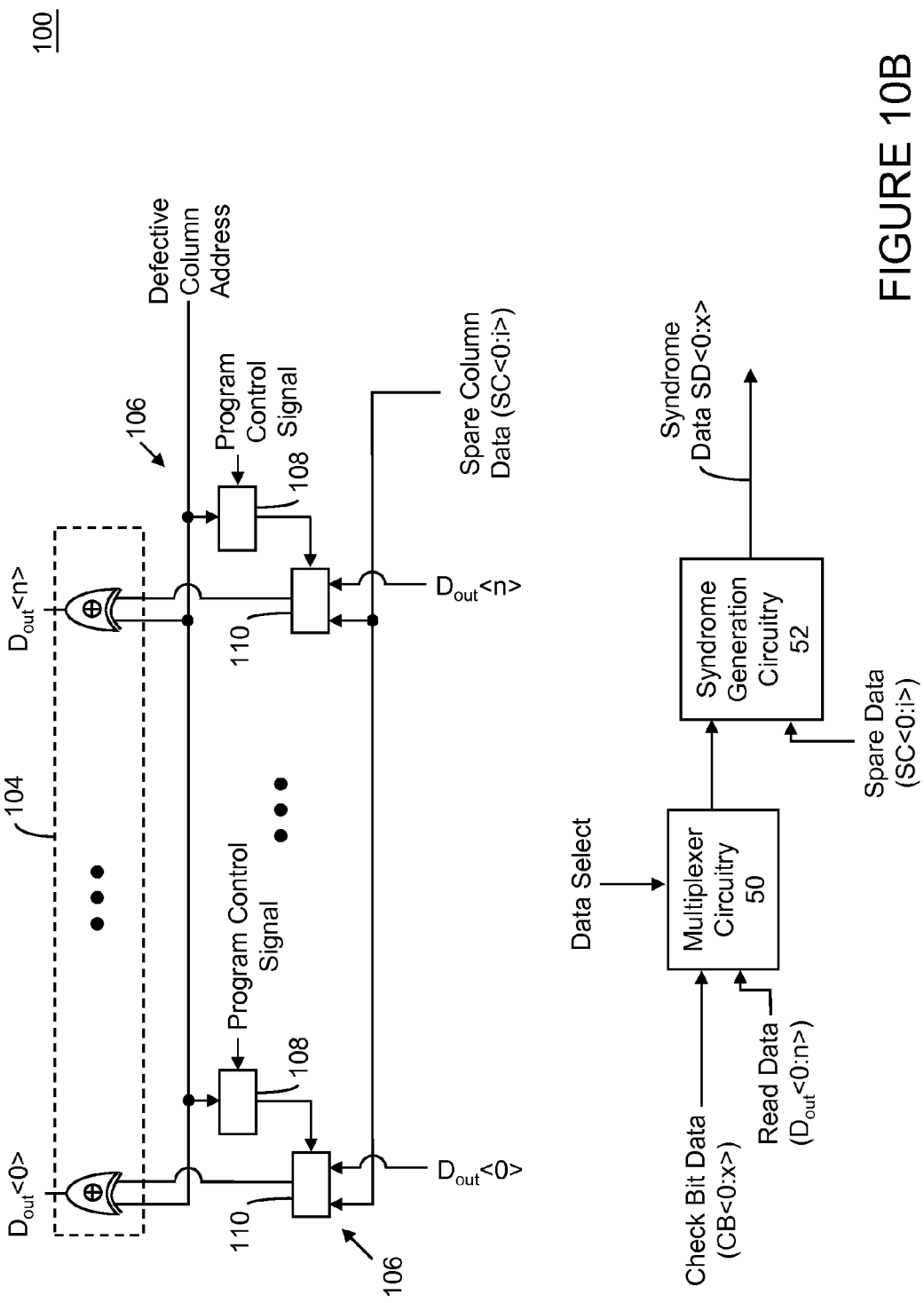
Figure 10C:
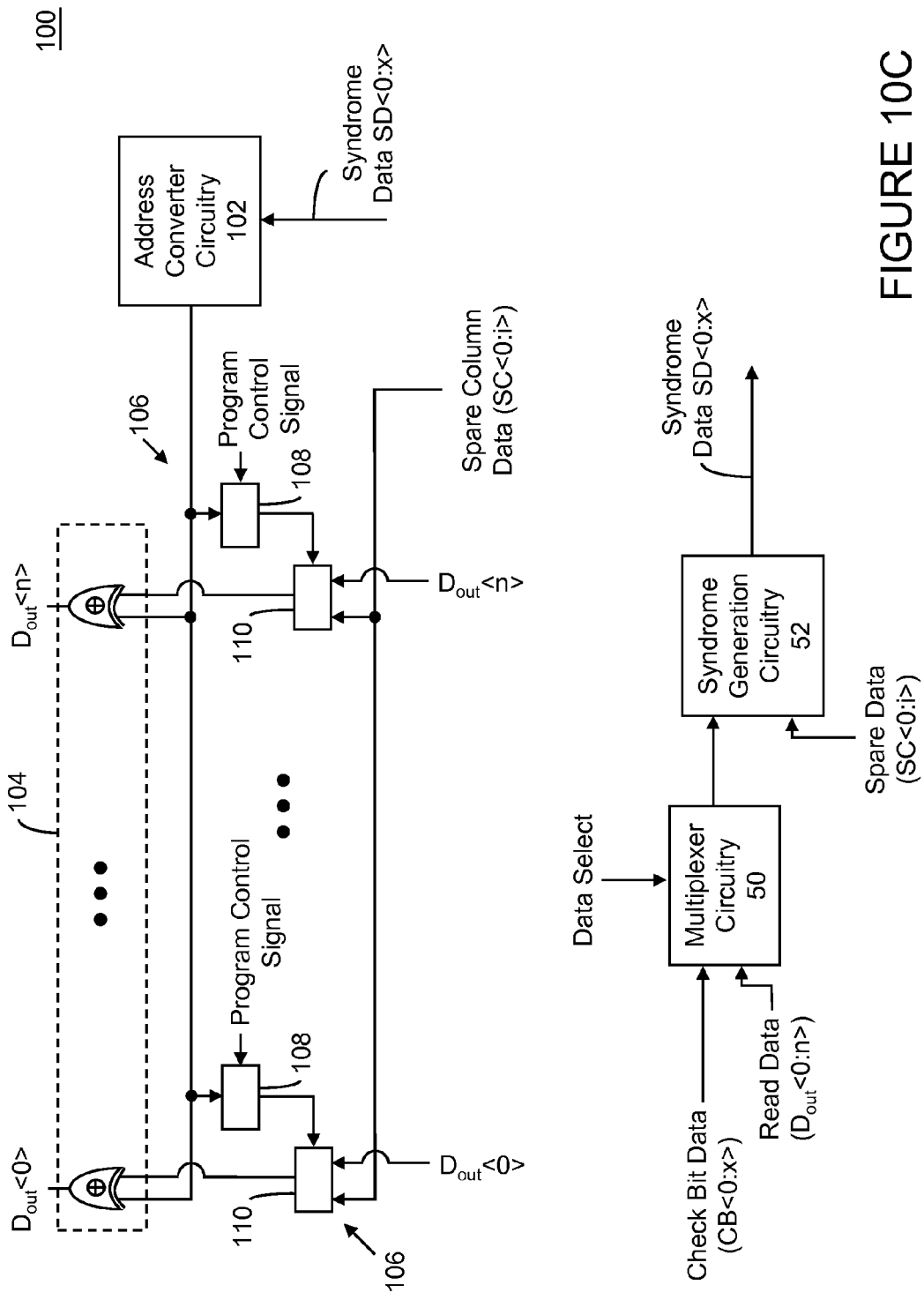
Figure 11A:
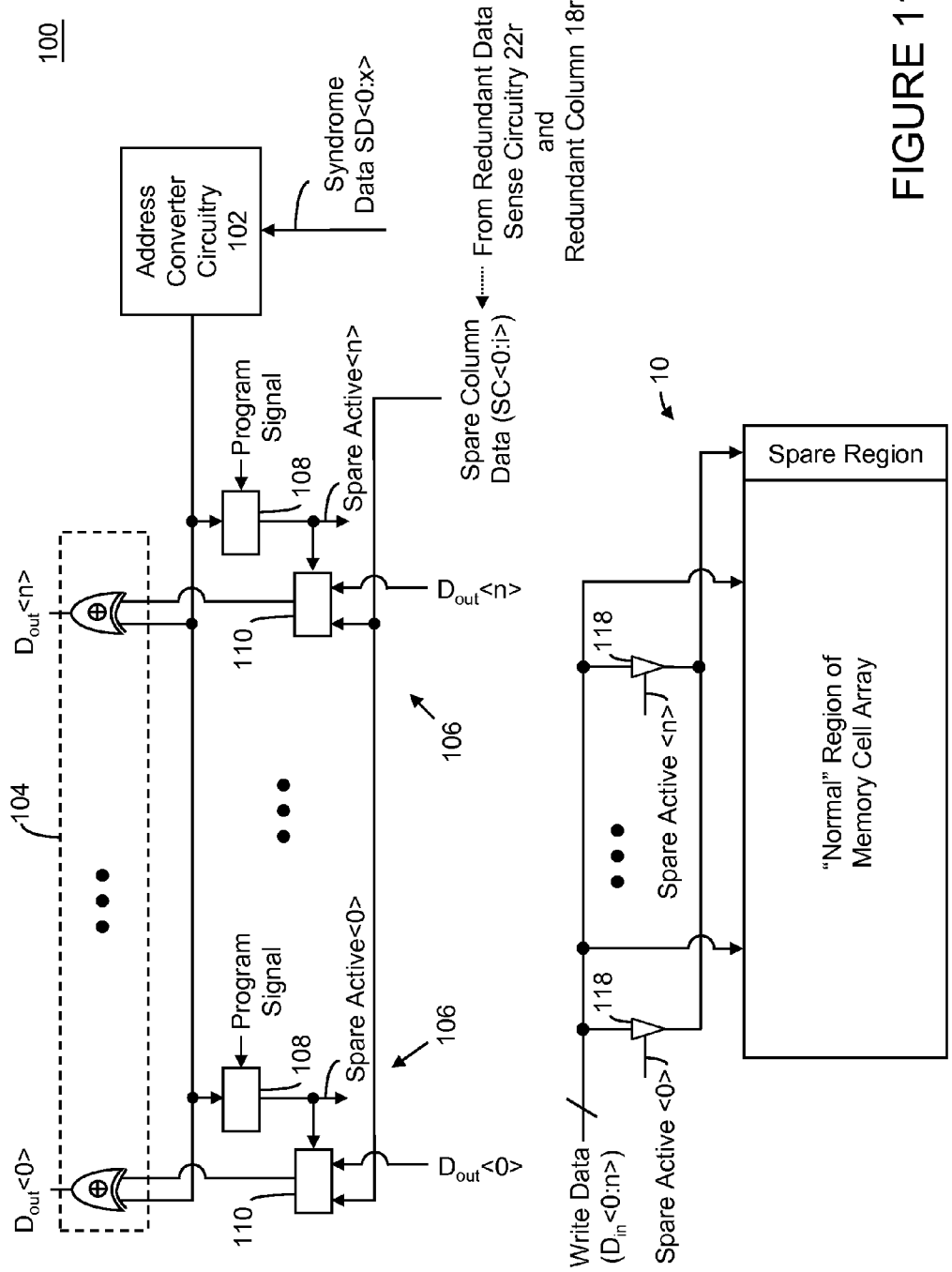
Figure 11B:
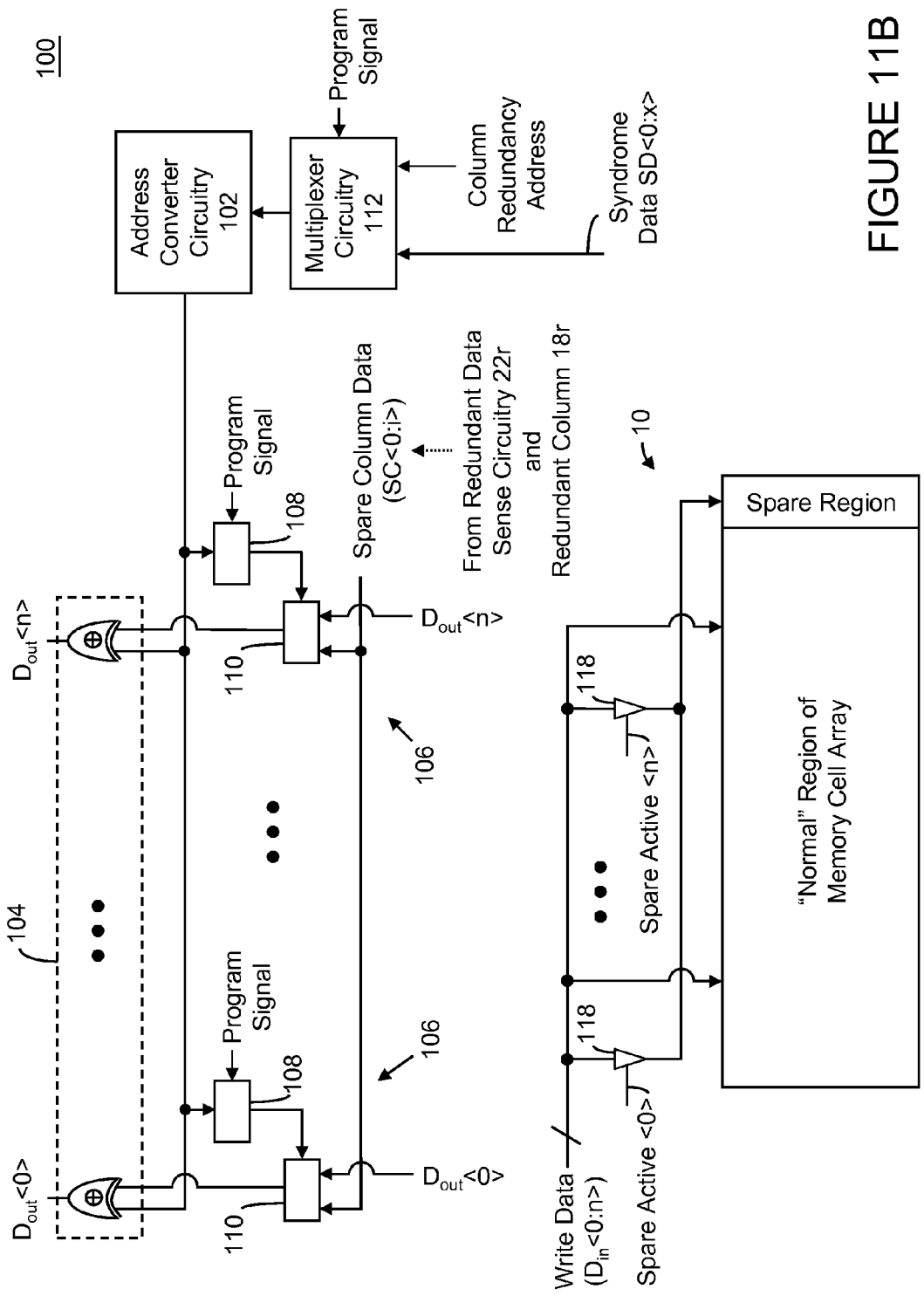
Figure 11C:
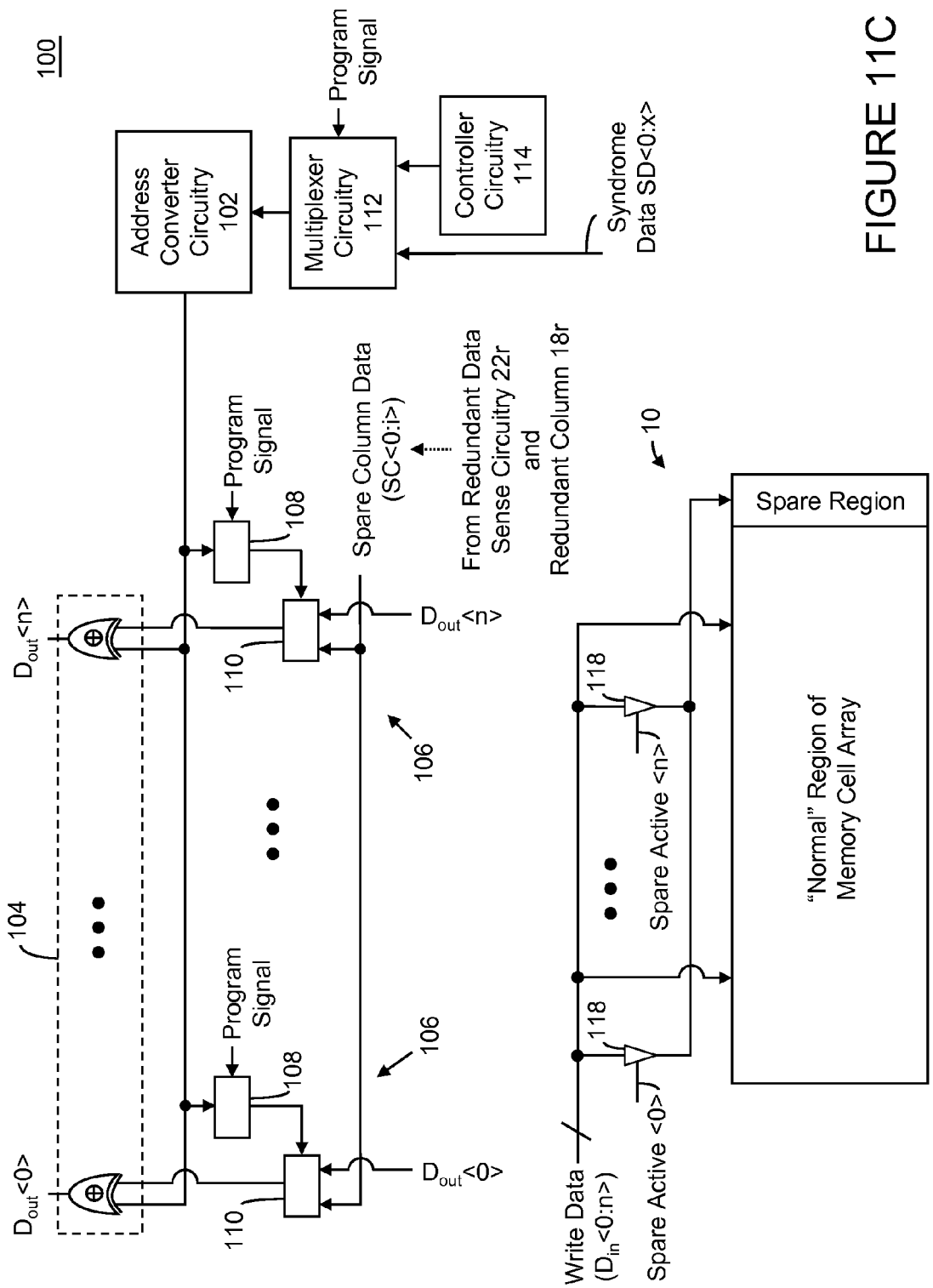

As mentioned above, the present inventions may be implemented in a logic device having a memory portion and logic portion (see, for example, FIGS. 8A and 8C), or an integrated circuit that is primarily a memory device (see, for example, FIG. 8B). The logic device may be, for example, a processor, controller, field programmable gate array, state machine, and/or a device including same. Indeed, the present inventions may be implemented in any device employing a memory array and redundancy and/or ECC architecture or technique.

Further, as mentioned above, the present inventions may be employed in conjunction with any memory cell technology now known or later developed. For example, the present inventions may be implemented in conjunction with a memory array, having a plurality of memory cells each including an electrically floating body transistor. (See, for example, (1) U.S. Pat. No. 6,969,662, (2) Okhonin et al., U.S. Patent Application Publication No. 2006/0131650 ("Bipolar Reading Technique for a Memory Cell Having an Electrically Floating Body Transistor"), (3) Okhonin et al., U.S. Patent Application Publication No. 2007/0058427 ("Memory Cell and Memory Cell Array Having an Electrically Floating Body Transistor, and Methods of Operating Same"), (4) Okhonin, U.S. patent application Ser. No. 11/633,311, filed Dec. 4, 2006, and entitled "Electrically Floating Body Memory Cell and Array, and Method of Operating or Controlling Same", and (5) Okhonin et al., U.S. patent application Ser. No. 11/703,429, filed on Feb. 7, 2007, and entitled "Multi-Bit Memory Cell Having Electrically Floating Body Transistor, and Method of Programming and Reading Same"). In this regard, the memory cell may consist of a PD or a FD SOI transistor (or transistor formed on or in bulk material/substrate) having a gate, which is disposed adjacent to the electrically floating body and separated therefrom by a gate dielectric. The body region of the transistor is electrically floating in view of the insulation or non-conductive region (for example, in bulk-type material/substrate) disposed beneath the body region. The state of memory cell is determined by the concentration of charge within the body region of the SOI transistor.

The memory cells of the memory cell array may be comprised of N-channel, P-channel and/or both types of transistors. Indeed, circuitry that is peripheral to the memory array (for example, sense amplifiers or comparators, row and column address decoders, as well as line drivers (not illustrated in detail herein)) may include P-channel and/or N-channel type transistors. Where N-channel type transistors or P-channel type transistors are employed as memory cells 12 in the memory array(s) 10, suitable write and read voltages are well known to those skilled in the art (and in view of the U.S. patents and U.S. patent applications incorporated herein by reference).

Moreover, the present inventions may be implemented in conjunction with any memory cell array configuration and/or arrangement of memory cell array 10. In this regard, integrated circuit device (for example, memory or logic device) may include a plurality of memory cell arrays, each having a plurality of memory cells, wherein certain of the circuitry (for example, address converter circuitry 102) is dedicated to one or more arrays and controller circuitry 114 is shared among the arrays.

In addition, the present inventions may be employed or implemented in conjunction with one or more of the memory cells, memory arrays, and techniques for programming, reading, controlling and/or operating a memory cell and array including, for example, (1) Okhonin et al., U.S. Patent Application Publication No. 2006/0131650 ("Bipolar Reading Technique for a Memory Cell Having an Electrically Floating Body Transistor"), (2) Okhonin et al., U.S. Patent Application Publication No. 2007/0058427 ("Memory Cell and Memory Cell Array Having an Electrically Floating Body Transistor, and Methods of Operating Same"), (3) Okhonin, U.S. patent application Ser. No. 11/633,311, filed Dec. 4, 2006, and entitled "Electrically Floating Body Memory Cell and Array, and Method of Operating or Controlling Same", and (4) Okhonin et al., U.S. patent application Ser. No. 11/703,429, filed on Feb. 7, 2007, and entitled "Multi-Bit Memory Cell Having Electrically Floating Body Transistor, and Method of Programming and Reading Same". The entire contents of these U.S. patent applications and publications, including, for example, the inventions, features, attributes, architectures, configurations, materials, techniques and advantages described and illustrated therein, are hereby incorporated by reference herein. For the sake of brevity, those discussions will not be repeated; rather those discussions (text and illustrations), including the discussions relating to the memory cell, architecture, layout, structure, are incorporated by reference herein in its entirety.

In addition, the memory cells may be arranged, configured and/or controlled using any of the memory cell arrays, architectures and/or control/operation techniques. For example, the memory cells may be arranged, configured and/or controlled using any of the memory cell arrays, architectures and/or control/operation techniques described and illustrated in the following U.S. patent applications:

(1) U.S. patent application Ser. No. 10/450,238, which was filed by Fazan et al. on Jun. 10, 2003, and entitled "Semiconductor Device" (now U.S. Pat. No. 6,969,662);
(2) U.S. patent application Ser. No. 10/487,157, which was filed by Fazan et al. on Feb. 18, 2004, and entitled "Semiconductor Device" (now U.S. Pat. No. 7,061,050);
(3) U.S. patent application Ser. No. 10/829,877, which was filed by Ferrant et al. on Apr. 22, 2004, and entitled "Semiconductor Memory Cell, Array, Architecture and Device, and Method of Operating Same" (now U.S. Pat. No. 7,085,153);
(4) U.S. patent application Ser. No. 10/840,009, which was filed by Ferrant et al. on May 6, 2004, and entitled "Semiconductor Memory Device and Method of Operating Same" (U.S. Patent Application Publication No. US 2004/0228168); and
(5) U.S. patent application Ser. No. 10/941,692, which was filed by Fazan et al. on Sep. 15, 2004, and entitled "Low Power Programming Technique for a One Transistor SOI Memory Device & Asymmetrical Electrically Floating Body Memory Device, and Method of Manufacturing Same" (now U.S. Pat. No. 7,184,298).

The entire contents of these five (5) U.S. patent applications, including, for example, the inventions, features, attributes, architectures, configurations, materials, techniques and advantages described and illustrated therein, are hereby incorporated by reference herein. For the sake of brevity, those discussions will not be repeated; rather those discussions (text and illustrations), including the discussions relating to the memory cell, architecture, layout, structure, are incorporated by reference.

Notably, the present inventions may be fabricated using well known techniques and/or materials. Indeed, any fabrication technique and/or material, whether now known or later developed, may be employed to fabricate the memory cells, transistors and/or memory array(s). For example, the present inventions may employ silicon (whether bulk-type or SOI), germanium, silicon/germanium, gallium arsenide or any other semiconductor material in which transistors may be formed. Indeed, the electrically floating body transistors, memory cells, and/or memory array(s) may employ the techniques described and illustrated in: 1.) U.S. patent application Ser. No. 10/884,481 (U.S. Patent Application Publication US 2005/0017240), by Fazan, entitled "Integrated Circuit Device, and Method of Fabricating Same", which was filed on Jul. 2, 2004; 2.) U.S. patent application Ser. No. 10/884,481 (U.S. Patent Application Publication US 2005/0017240); 3.) and/or U.S. patent application Ser. No. 11/580,169, by Bassin, entitled "One Transistor Memory Cell having a Strained Electrically Floating Body Region, and Method of Operating Same", which was filed on Oct. 12, 2006, and (hereinafter collectively "Integrated Circuit Device Patent Applications"). The entire contents of the Integrated Circuit Device Patent Applications, including, for example, the inventions, features, attributes, architectures, configurations, materials, techniques and advantages described and illustrated therein, are hereby incorporated by reference herein.

Further, in one embodiment, an integrated circuit device includes memory section (having a plurality of memory cells, for example, PD or FD SOI memory transistors) and logic section (having, for example, high performance transistors, such as FinFET, multiple gate transistors, and/or non-high performance transistors (for example, single gate transistors that do not possess the performance characteristics of high performance transistors—not illustrated)). Moreover, as noted above, the memory cell and/or memory cell array, as well as the circuitry of the present inventions may be implemented in an integrated circuit device having a memory portion and a logic portion (see, for example, FIG. 8A), or an integrated circuit device that is primarily a memory device (see, for example, FIG. 8B). The memory array may include a plurality of memory cells arranged in a plurality of rows and columns wherein each memory cell includes a transistor (whether fabricated in a bulk-type material or SOI material), for example, an electrically floating body transistor. The memory arrays may be comprised of N-channel, P-channel and/or both types of transistors. Indeed, circuitry that is peripheral to the memory array (for example, data sense circuitry (for example, sense amplifiers or comparators), memory cell selection and control circuitry (for example, word line and/or source line drivers), as well as row and column address decoders) may include P-channel and/or N-channel type transistors.

The present inventions may be employed with other redundancy and/or ECC circuitry. For example, the present inventions may be implemented in conjunction with row redundancy circuitry including, for example, U.S. patent application Ser. No. 11/804,098, by Singh, entitled "Integrated Circuit Having Memory Array Including Row Redundancy, and Method of Programming, Controlling and/or Operating Same", which was filed on May 17, 2007, the contents of which are incorporated by reference herein.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the embodiments, features, attributes and advantages of the inventions described and illustrated herein are not exhaustive and it should be understood that such other, similar, as well as different, embodiments, features, attributes and advantages of the present inventions are within the scope of the present inventions.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the embodiments, features, attributes and advantages of the inventions described and illustrated herein are not exhaustive and it should be understood that such other, similar, as well as different, embodiments, features, attributes and advantages of the present inventions are within the scope of the present inventions.

For example, the programming of the redundancy circuitry (for example, by controller circuitry 114) may be a one-time process, for example, during start-up/power-up and/or during an initialization sequence. The programming may also be in situ, for example, in response to detection of a bit failure or anticipated bit failure by controller circuitry 114, for example, during operation of the memory cell array 10.

For example, logic circuitry 104 may be any type of circuitry (whether hardwired or programmed), whether now known or later developed, that performs ECC operations. In one embodiment, a plurality of logic gates (for example, AND or NAND) may be employed.

The above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof (See, for example, FIGS. 10A-10C and 11A-11C). For the sake of brevity, many of those permutations and combinations are not discussed separately herein.

Further, the above embodiments of the present inventions are merely exemplary embodiments. They are not intended to be exhaustive or to limit the inventions to the precise forms, techniques, materials and/or configurations disclosed. Many modifications and variations are possible in light of the above teaching. It is to be understood that other embodiments may be utilized and operational changes may be made without departing from the scope of the present inventions. As such, the foregoing description of the exemplary embodiments of the inventions has been presented for the purposes of illustration and description. Many modifications and variations are possible in light of the above teaching. It is intended that the scope of the inventions not be limited solely to the description above.

Notably, in certain illustrations, output logic gates 104 are generally illustrated as XOR gate logic. The output logic gates may be any type of circuitry and/or logic, whether now known or later developed; all such circuitry is intended to fall within the scope of the present inventions.

It should be further noted that the term "circuit" may mean, among other things, a single component (for example, electrical/electronic and/or microelectromechanical) or a multiplicity of components (whether in integrated circuit form or otherwise), which are active and/or passive, and which are coupled together to provide or perform a desired function. The term "circuitry" may mean, among other things, a circuit (whether integrated or otherwise), a group of such circuits, one or more processors, one or more state machines, one or more processors implementing software, or a combination of one or more circuits (whether integrated or otherwise), one or more state machines, one or more processors, and/or one or more processors implementing software. The term "data" may mean, among other things, a current or voltage signal(s) whether in an analog or a digital form.

The above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

The invention claimed is:

1. An integrated circuit device comprising:
   a memory cell array comprising a plurality of memory cells arranged in a matrix of rows and columns, wherein the columns comprise a plurality of normal columns and at least one redundant column;
   multiplexer circuitry coupled to the memory cell array, wherein the multiplexer circuitry comprises a plurality of data multiplexers, wherein each data multiplexer comprises a plurality of inputs and an associated output to responsively output data from one of the plurality of inputs, wherein the plurality of inputs comprise: (i) a first input to receive write data; and (ii) a second input to receive read data; and
   syndrome generation circuitry, coupled to the multiplexer circuitry, to generate: (i) a write data syndrome vector using the write data; and (ii) a read data syndrome vector using the read data, wherein at least one of the write data syndrome vector and the read data syndrome vector determine a use of the plurality of normal columns and the at least one redundant column.

2. The integrated circuit device of claim 1 wherein the write data is representative of data to be written into memory cells of the memory cell array in response to a write operation.

3. The integrated circuit device of claim 1 wherein the read data is representative of data read from memory cells of the memory cell array in response to a read operation.

4. The integrated circuit device of claim 1 wherein the syndrome generation circuitry comprises a plurality of XOR logic gates.

5. The integrated circuit device of claim 4 wherein the plurality of XOR logic gates is arranged in a logic tree architecture comprising first, second and third levels of XOR logic, wherein:
the first level of XOR logic comprises inputs to receive the outputs of the plurality of data multiplexers;
the second level of XOR logic comprises inputs to receive the outputs of the first level of XOR logic; and
the third level of XOR logic comprises inputs to receive the outputs of the second level of XOR logic.

6. The integrated circuit device of claim 4 wherein the plurality of XOR logic gates is arranged in a logic tree architecture comprising a plurality of levels of XOR logic levels, wherein a Nth level of XOR logic comprises: (i) inputs to receive the outputs of a preceding level of XOR logic gates and data from the at least one redundant column; and (ii) an output that is the read data syndrome vector.

7. The integrated circuit device of claim 1 wherein:
the multiplexer circuitry further comprises a plurality of check bit multiplexers, each check bit multiplexer having a plurality of inputs, comprising: (i) a first input to receive check bit data; and (ii) a second input to receive a predetermined data, and an associated output to responsively output data from one of the plurality of inputs; and
the syndrome generation circuitry generates: (i) a write data syndrome vector using the write data and the predetermined value; and (ii) a read data syndrome vector using the read data and the check bit data.

8. The integrated circuit device of claim 7 wherein the syndrome generation circuitry comprises a plurality of XOR logic gates.

9. The integrated circuit device of claim 8 wherein the plurality of XOR logic gates is arranged in a logic tree architecture comprising first, second and third levels of XOR logic, wherein:
the first level of XOR logic comprises inputs to receive the outputs of the plurality of data multiplexers;
the second level of XOR logic comprises inputs to receive the outputs of the first level of XOR logic; and
the third level of XOR logic comprises inputs to receive the outputs of the second level of XOR logic.

10. The integrated circuit device of claim 8 wherein the plurality of XOR logic gates is arranged in a logic tree architecture comprising a plurality of levels of XOR logic levels, wherein a Nth level of XOR logic comprises: (i) inputs to receive the outputs of a preceding level of XOR logic gates and data from the at least one redundant column; and (ii) an output that is the read data syndrome vector.

11. The integrated circuit device of claim 1 wherein the write data syndrome vector is stored in memory as check bit data.

12. The integrated circuit device of claim 1 wherein the plurality of normal columns are selectable via normal column address data, and the at least one redundant column is selectable via a redundant column address data.

13. The integrated circuit device of claim 12 further comprising address converter circuitry, coupled to the syndrome generation circuitry, to generate defective column address data, which is representative of a physical bit location of a defective column, using the read data syndrome vector.

14. The integrated circuit device of claim 13 further comprising a defective column address memory, coupled to the address converter circuitry, to store the defective column address data.

15. The integrated circuit device of claim 14 wherein the memory permanently stores the defective column address data.

16. The integrated circuit device of claim 13 further comprising a plurality of redundancy program circuits that are coupled to the memory array to receive the read data and spare column data, which is representative of data read from memory cells associated with the at least one redundant column of the memory cell array, wherein each redundancy program circuit outputs: (i) read data which is associated with one of a normal column; or (ii) the spare column data, and wherein when one of a normal column address data corresponds to the defective column address data, the redundancy program circuit associated therewith outputs the defective column address data.

17. The integrated circuit device of claim 16 wherein each redundancy program circuit comprises:
a multiplexer having a plurality of inputs comprising: (i) a first input to receive read data which is associated with one of a normal column; and (ii) a second input to receive the spare column data, and an associated output to responsively output data from one of the plurality of inputs; and
a memory, coupled to an associated multiplexer, to store spare column control data which controls the associated multiplexer.

18. The integrated circuit device of claim 17 wherein the memory of each redundancy program circuit is coupled to the address converter circuitry and, in response to a program signal, the memory of the redundancy program circuit which is associated with the normal column that corresponds to the defective column address data stores the spare column control data.

19. The integrated circuit device of claim 17 wherein the memory, in response to a program signal, stores the spare column control data.

20. The integrated circuit device of claim 16 further including a plurality of logic gates having a first input to receive an output of an associated redundancy program circuit and a second input to receive correction data wherein when the read data includes one or more errors therein, the one or more logic gates which receives read data having an error corrects the read data using the correction data.

21. The integrated circuit device of claim 20 wherein each logic gate of the plurality of logic gates includes an XOR logic gate.

* * * * *

UNITED STATES PATENT AND TRADEMARK OFFICE
CERTIFICATE OF CORRECTION

PATENT NO. : 8,402,326 B2  
APPLICATION NO. : 13/306642  
DATED : March 19, 2013  
INVENTOR(S) : Anant Pratap Singh Page 1 of 1

It is certified that error appears in the above-identified patent and that said Letters Patent is hereby corrected as shown below:

On Title Page, Item (54) and in the specification, column 1, line 3, "Title", delete "REDUNDANCY" and insert -- REDUNDANCY, --, therefor.

Signed and Sealed this
Twenty-eighth Day of May, 2013

Teresa Stanek Rea
*Acting Director of the United States Patent and Trademark Office*